US012350286B2

(12) United States Patent
Patel et al.

(10) Patent No.: US 12,350,286 B2
(45) Date of Patent: Jul. 8, 2025

(54) POLYPEPTIDES DIRECTED AGAINST VIRAL INFECTION AND USES THEREOF

(71) Applicant: QUADRUMIX BIOTECHNOLOGY INC., Lethbridge (CA)

(72) Inventors: Trushar R. Patel, Lethbridge (CA); Carla Stephanie Coffin, Calgary (CA); Vanessa Meier-Stephenson, Calgary (CA); Maulik D. Badmalia, Lethbridge (CA)

(73) Assignee: QUADRUMIX BIOTECHNOLOGY INC., Alberta (CA)

( * ) Notice: Subject to any disclaimer, the term of this patent is extended or adjusted under 35 U.S.C. 154(b) by 780 days.

(21) Appl. No.: 17/425,791

(22) PCT Filed: Feb. 25, 2021

(86) PCT No.: PCT/CA2021/050234
§ 371 (c)(1),
(2) Date: Jul. 26, 2021

(87) PCT Pub. No.: WO2021/168575
PCT Pub. Date: Sep. 2, 2021

(65) Prior Publication Data
US 2023/0218656 A1 Jul. 13, 2023

Related U.S. Application Data

(60) Provisional application No. 62/982,474, filed on Feb. 27, 2020.

(51) Int. Cl.
*A61K 31/713* (2006.01)
*A61K 47/68* (2017.01)
*A61P 31/20* (2006.01)

(52) U.S. Cl.
CPC ........ *A61K 31/713* (2013.01); *A61K 47/6839* (2017.08); *A61P 31/20* (2018.01)

(58) Field of Classification Search
CPC .... A61K 31/713; A61K 47/6839; A61P 31/20
See application file for complete search history.

(56) References Cited

U.S. PATENT DOCUMENTS 6,559,279 B1 * 5/2003 Manoharan .......... C07K 14/003 536/25.31
6,969,584 B2 * 11/2005 Nolan ................ C12N 15/1075 435/5
9,562,076 B2 * 2/2017 Mier .................... A61K 47/544
2016/0122420 A1 * 5/2016 Rowlands .......... G01N 33/6857 435/69.3
2019/0177710 A1 * 6/2019 Lee ........................ C12N 15/11
2019/0307798 A1 * 10/2019 Kruse ..................... A61P 31/20
2020/0095605 A1 * 3/2020 Watson .................. A61K 47/64
2023/0041178 A1 * 2/2023 Bermingham ..... C12N 15/1137
2024/0132877 A1 * 4/2024 Cotta-Ramusino .......................... A61K 31/7088
2024/0141358 A1 * 5/2024 Ward ................. C12N 15/1138
2024/0228573 A9 * 7/2024 Kakimoto ................ C07K 1/18

FOREIGN PATENT DOCUMENTS

WO WO-0227031 A2 * 4/2002 ........... C12Q 1/6897
WO WO-2009092612 A1 * 7/2009 ........... A61K 38/162

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10 (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14 (Year: 2000).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714 (Year: 2015).*
Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*
Sela-Culang I, Kunik V, Ofran Y. The structural basis of antibody-antigen recognition. Front Immunol. Oct. 8, 2013;4:302. (Year: 2013).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Collis, A. V., Brouwer, A. P., & Martin, A. C. (2003). Analysis of the antigen combining site: correlations between length and sequence composition of the hypervariable loops and the nature of the antigen. Journal of molecular biology, 325(2), 337-354. (Year: 2003).*
Figueroa, G. B. et al. (2024). Development of a single-domain antibody to target a G-quadruplex located on the hepatitis B virus covalently closed circular DNA genome. Journal of Medical Virology, 96(6), e29692-n/a (Year: 2024).*
Wesolowski, J. et al. (2009). Single domain antibodies: promising experimental and therapeutic tools in infection and immunity. Medical Microbiology and Immunology, 198(3), 157-174. (Year: 2009).*

(Continued)

*Primary Examiner* — Janet L Andres
*Assistant Examiner* — Carey Alexander Stuart
(74) *Attorney, Agent, or Firm* — Sheridan Ross P.C.

(57) ABSTRACT

According to embodiments, at least one polypeptide comprising at least one antiviral single domain antibody and their methods of use in antiviral treatment are provided. More specifically, embodiments provide at least one polypeptide having at least one anti-viral single domain antibody (e.g. anti-Hepatitis B Virus) for targeting a guanine-rich region of the viral DNA, inhibiting transcription of the viral DNA.

25 Claims, 13 Drawing Sheets

Specification includes a Sequence Listing.

(56) References Cited

OTHER PUBLICATIONS

Kim, S. W., Yoon, J. S., Lee, M., & Cho, Y. (2022). Toward a complete cure for chronic hepatitis B: Novel therapeutic targets for hepatitis B virus. Clinical and molecular hepatology, 28(1), 17-30. (Year: 2022).*

Asadi-Asadabad, S. et al. (2021). Influence of Pattern Recognition Receptor Ligands on Induction of Innate Immunity and Control of Hepatitis B Virus Infection. Viral immunology, 34(8), 531-541. (Year: 2021).*

Schaffitzel, C.; Berger, I.; Postberg, J.; Hanes, J.; Lipps, H.J.; Plückthun, A. In vitro generated antibodies specific for telomeric guanine-quadruplex DNA react with Stylonychia lemnae macronuclei. Proc. Natl. Acad. Sci. USA; 2001; 98, pp. 8572-8577. (Year: 2001).*

Biffi, G.; Tannahill, D.; McCafferty, J.; Balasubramanian, S. Quantitative visualization of DNA G-quadruplex structures in human cells. Nat. Chem.; 2013; 5, pp. 182-186. (Year: 2013).*

Suslov, A., Meier, M. A., Ketterer, S., Wang, X., Wieland, S., & Heim, M. H. (2021). Transition to HBeAg-negative chronic hepatitis B virus infection is associated with reduced cccDNA transcriptional activity. Journal of hepatology, 74(4), 794-800. (Year: 2021).*

Fung, S., Choi, H. S. J., Gehring, A., & Janssen, H. L. A. (2022). Getting to HBV cure: The promising paths forward. Hepatology (Baltimore, Md.), 76(1), 233-250. (Year: 2022).*

Lucifora, J., & Zoulim, F. (2011). The life cycle of hepatitis B virus and antiviral targets. Future Virology, 6(5), 599-614. (Year: 2011).*

Serruys et al. "Production, characterization and in vitro testing of HBcAg-specific VHH intrabodies," Journal of General Virology, Mar. 2010, vol. 91, Pt. 3, pp. 643-652.

Walsh et al. "Targeting the hepatitis B virus precore antigen with a novel IgNAR single variable domain intrabody," Virology, Mar. 2011, vol. 411, No. 1, pp. 132-141.

Zhu et al. "HBV cccDNA and Its Potential as a Therapeutic Target," Journal of Clinical and Translational Hepatology, Sep. 2019, vol. 7, No. 3, pp. 258-262.

International Search Report and Written Opinion for International (PCT) Patent Application No. PCT/CA2021/05234, dated May 10, 2021, 7 pages.

* cited by examiner

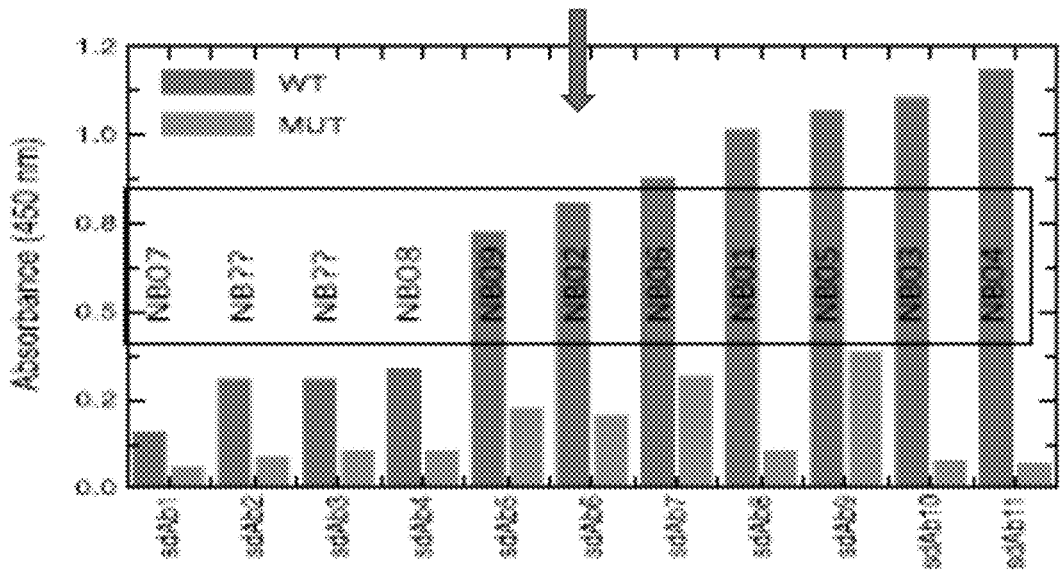

*Figure 4A*

| Single Domain Antibody (sdAb) | Constituent Protein Sequence |
| --- | --- |
| sdAb 1 | MAEVQLQASGGGFVQPGGSLRLSCAASGRTYRHSGMGWFRQAPGKEREFVSAISDDHNMESYYADSVKGRFT ISRDNSKNTVYLQMNSLRAEDTATYYCAMTKWHGPSGPWYWGQGTQVTVSS |
| sdAb 4 | MAEVQLQASGGGFVZPGGSLRLSCAASGRTSKWYSMGWFRQAPGKEREFVSAISYRQNIEAYYADSVKGRFT ISRDNSKNTVYLQMNSLRAEDTATYYCAATHSYLPKFPTHFPQPQDYWGQGTQVTVSS |
| sdAb 5 | MAEVQLQASGGGFVZPGGSLRLSCAASGRTSYHTNMGWFRQAPGKEREFVSAISSSPNAATYYADSVKGRFT ISRDNSKNTVYLQMNSLRAEDTATYYCARTKYGRVMGHMWYWGQGTQVTVSS |
| sdAb 6 | MAEVQLQASGGGFVQPGGSLRLSCAASGTGFRHTAMGWFRQAPGKEREFVSAISGHASKQAYYADSVKGRFT ISRDNSKNTVYLQMNSLPAEDTATYYCAFRPAEKIYGHPMAPQKLWYWGQGTQVTVSS |
| sdAb 7 | MAEVQLQASGGGFVQPGSLRLSCAASGRTYRSETMGWFRQAPGKEREFVSAISWGWSNRAYYADSVKGRFT ISRDNSKNTVYLQMNSLPAEDTATYYCASRHMRPAPWSGFGMSYWGQGTQVTVSS |
| sdAb 8 | MAEVQLQASGGGFVQPGGSLRLSCAASGTTSGQTAMGWFRQAPGKEREFVSAISGHHTPRAYYADSVKGRFT ISRDNSKNTVYLQMNSLRAEDTATYYCAWIRRKFQSWYWGQGTQVTVSS |
| sdAb 9 | MAEVQLQASGGGFVQPGSLRLSCAASGRTSGHYSMGRFRQAPGKEREFVSAISGRGNSLSYYADSVKGRFT ISRDNSKNTVYLQMNSLRAEDTATYYCAWNHRDSHPQSGKHMRYWGQGTQVTVSS |
| sdAb10 | MAEVQLQASGGGFVQPGGSLRLSCAASGRTSKITSMGWFRQAPGKEREFVSAISWSNGLTNYYADSVKGRFT ISRDNSKNTVYLQMNSLRAEDTATYYCASKIHTKPKWYWGQGTQVTVSS |
| sdAb 11 | MAEVQLQASGGGFVQPGGSLRLSCAASGFTSESTSMGWFRQAPGKEREFVSAISRWESTEEYYADSVKGRFT ISRDNSKNTVYLQMNSLRAEDTATYYCAYPMHWGGRWRWNYWGQGTQVTVSS |

*Figure 4B* sdAb 10-01
GRKKRRQRRRPPQ-GGGGS-sdAb10_sequence-GGGGS-*NPLGFFP*-GGGGS-DHQLD-GGGGS-PKKKRKV-SSFLRN-His6 tag
sdAb 10-02
sdAb10_sequence-GGGGS-GRKKRRQRRRPPQ-GGGGS-*NPLGFFP*-GGGGS-DHQLD-GGGGS-PKKKRKV-SSFLRN-His6 tag
*Figure 6A*
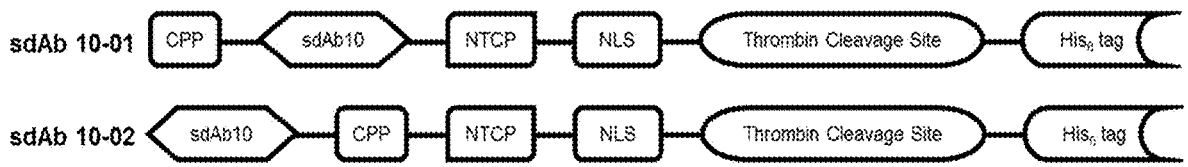
*Figure 6B*
*Figure 6C*

SEQUENCE LISTING

```
<160> NUMBER OF SEQ ID NOS: 20

<210> SEQ ID NO 1
<211> LENGTH: 23
<212> TYPE: DNA
<213> ORGANISM: Hepatitis B virus
<220> FEATURE:
<221> NAME/KEY: misc_feature
<223> OTHER INFORMATION: Wild-Type G-Rich Sequence from Pre-Core
      Promoter of Hepatitis B virus cccDNA (Residues 1732 - 1754)

<400> SEQUENCE: 1
ctgggaggag ctgggggagg aga                                           23

<210> SEQ ID NO 2
<211> LENGTH: 23
<212> TYPE: DNA
<213> ORGANISM: Artificial sequence
<220> FEATURE:
<223> OTHER INFORMATION: Mutant G-Rich Sequence from Pre-Core Promoter
      of Hepatitis B virus cccDNA

<400> SEQUENCE: 2
ctgggaggag ctggggaagg aga                                           23

<210> SEQ ID NO 3
<211> LENGTH: 13
<212> TYPE: PRT
<213> ORGANISM: Homo sapiens
<220> FEATURE:
<221> NAME/KEY: MISC_FEATURE
<223> OTHER INFORMATION: Cell Penetrating Peptide

<400> SEQUENCE: 3

Gly Arg Lys Lys Arg Arg Gln Arg Arg Arg Pro Pro Gln
1               5                   10

<210> SEQ ID NO 4
<211> LENGTH: 7
<212> TYPE: PRT
<213> ORGANISM: Hepatitis B virus
<220> FEATURE:
<221> NAME/KEY: MISC_FEATURE
<223> OTHER INFORMATION: Hepatitis B virus preS1 Protein Peptide
      (Residues 18 - 24)

<400> SEQUENCE: 4

Asn Pro Leu Gly Phe Phe Pro
1               5

<210> SEQ ID NO 5
<211> LENGTH: 5
<212> TYPE: PRT
<213> ORGANISM: Hepatitis B virus
<220> FEATURE:
<221> NAME/KEY: MISC_FEATURE
<223> OTHER INFORMATION: Hepatitis B virus preS1 Protein Peptide
      (Residues 25 - 29)

<400> SEQUENCE: 5

Asp His Gln Leu Asp
1               5

<210> SEQ ID NO 6
<211> LENGTH: 7
<212> TYPE: PRT
<213> ORGANISM: Simian virus 40
<220> FEATURE:
```

```
<221> NAME/KEY: MISC_FEATURE
<223> OTHER INFORMATION: Nuclear Localization Sequence

<400> SEQUENCE: 6

Pro Lys Lys Lys Arg Lys Val
1               5

<210> SEQ ID NO 7
<211> LENGTH: 5
<212> TYPE: PRT
<213> ORGANISM: Artificial sequence
<220> FEATURE:
<223> OTHER INFORMATION: Poly-Glycine-Serine Linker

<400> SEQUENCE: 7

Gly Gly Gly Gly Ser
1               5

<210> SEQ ID NO 8
<211> LENGTH: 6
<212> TYPE: PRT
<213> ORGANISM: Artificial sequence
<220> FEATURE:
<223> OTHER INFORMATION: Thrombin Cleavage Site

<400> SEQUENCE: 8

Ser Ser Phe Leu Arg Asn
1               5

<210> SEQ ID NO 9
<211> LENGTH: 124
<212> TYPE: PRT
<213> ORGANISM: Artificial sequence
<220> FEATURE:
<223> OTHER INFORMATION: Single-Domain Antibody 1

<400> SEQUENCE: 9

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Tyr Arg
            20                  25                  30

His Ser Gly Met Gly Trp Phe Arg Gln Ala Pro Gly Lys Glu Arg Glu
        35                  40                  45

Phe Val Ser Ala Ile Ser Asp Asp His Asn Met Glu Ser Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Met Thr Lys Trp His Gly Pro Gly Pro His Trp
            100                 105                 110

Tyr Trp Gly Gln Gly Thr Gln Val Thr Val Ser Ser
        115                 120

<210> SEQ ID NO 10
<211> LENGTH: 130
<212> TYPE: PRT
<213> ORGANISM: Artificial sequence
<220> FEATURE:
<223> OTHER INFORMATION: Single-Domain Antibody 4

<400> SEQUENCE: 10

Met Ala Glu Val Gln Leu Gln Ala Ser Gly Gly Gly Phe Val Glx Pro
```

```
              1               5                  10                 15
Gly Gly Ser Leu Arg Leu Ser Cys Ala Ala Ser Gly Arg Thr Ser Lys
            20                  25                 30

Trp Tyr Ser Met Gly Trp Phe Arg Gln Ala Pro Gly Lys Glu Arg Glu
            35                  40                 45

Phe Val Ser Ala Ile Ser Tyr Arg Gln Asn Ile Arg Ala Tyr Tyr Ala
            50                  55                 60

Asp Ser Val Lys Gly Arg Phe Thr Ile Ser Arg Asp Asn Ser Lys Asn
65                  70                  75                     80

Thr Val Tyr Leu Gln Met Asn Ser Leu Arg Ala Glu Asp Thr Ala Thr
                85                  90                 95

Tyr Tyr Cys Ala Ala Thr His Ser Tyr Leu Phe Lys Phe Pro Thr His
                100                 105                110

Phe Pro Gln Pro Gln Asp Tyr Trp Gly Gln Gly Thr Gln Val Thr Val
                115                 120                125

Ser Ser
    130
```

<210> SEQ ID NO 11
<211> LENGTH: 124
<212> TYPE: PRT
<213> ORGANISM: Artificial sequence
<220> FEATURE:
<223> OTHER INFORMATION: Single-Domain Antibody 5

<400> SEQUENCE: 11

```
Met Ala Glu Val Gln Leu Gln Ala Ser Gly Gly Gly Phe Val Glx Pro
1               5                   10                 15

Gly Gly Ser Leu Arg Leu Ser Cys Ala Ala Ser Gly Arg Thr Ser Tyr
            20                  25                 30

His Thr Asn Met Gly Trp Phe Arg Gln Ala Pro Gly Lys Glu Arg Glu
            35                  40                 45

Phe Val Ser Ala Ile Ser Ser Ser Pro Asn Ala Ala Thr Tyr Tyr Ala
            50                  55                 60

Asp Ser Val Lys Gly Arg Phe Thr Ile Ser Arg Asp Asn Ser Lys Asn
65                  70                  75                     80

Thr Val Tyr Leu Gln Met Asn Ser Leu Arg Ala Glu Asp Thr Ala Thr
                85                  90                 95

Tyr Tyr Cys Ala Arg Thr Lys Tyr Gly Arg Val Met Gly His Met Trp
                100                 105                110

Tyr Trp Gly Gln Gly Thr Gln Val Thr Val Ser Ser
                115                 120
```

<210> SEQ ID NO 12
<211> LENGTH: 130
<212> TYPE: PRT
<213> ORGANISM: Artificial sequence
<220> FEATURE:
<223> OTHER INFORMATION: Single-Domain Antibody 6

<400> SEQUENCE: 12

```
Met Ala Glu Val Gln Leu Gln Ala Ser Gly Gly Gly Phe Val Gln Pro
1               5                   10                 15

Gly Gly Ser Leu Arg Leu Ser Cys Ala Ala Ser Gly Thr Gly Phe Arg
            20                  25                 30

His Thr Ala Met Gly Trp Phe Arg Gln Ala Pro Gly Lys Glu Arg Glu
            35                  40                 45
```

```
Phe Val Ser Ala Ile Ser Gly His Ala Ser Lys Gln Ala Tyr Tyr Ala
         50                  55                  60
Asp Ser Val Lys Gly Arg Phe Thr Ile Ser Arg Asp Asn Ser Lys Asn
 65                  70                  75                  80
Thr Val Tyr Leu Gln Met Asn Ser Leu Arg Ala Glu Asp Thr Ala Thr
                 85                  90                  95
Tyr Tyr Cys Ala Phe Arg Arg Ala Glu Lys Ile Tyr Gly His Pro Met
                100                 105                 110
Ala Pro Gln Lys Leu Trp Tyr Trp Gly Gln Gly Thr Gln Val Thr Val
                115                 120                 125
Ser Ser
130
```

<210> SEQ ID NO 13
<211> LENGTH: 127
<212> TYPE: PRT
<213> ORGANISM: Artificial sequence
<220> FEATURE:
<223> OTHER INFORMATION: Single-Domain Antibody 7

<400> SEQUENCE: 13

```
Met Ala Glu Val Gln Leu Gln Ala Ser Gly Gly Gly Phe Val Gln Pro
 1               5                  10                  15
Gly Gly Ser Leu Arg Leu Ser Cys Ala Ala Ser Gly Arg Thr Tyr Arg
                 20                  25                  30
Gly Glu Thr Met Gly Trp Phe Arg Gln Ala Pro Gly Lys Glu Arg Glu
                 35                  40                  45
Phe Val Ser Ala Ile Ser Trp Gly Trp Ser Asn Arg Ala Tyr Tyr Ala
         50                  55                  60
Asp Ser Val Lys Gly Arg Phe Thr Ile Ser Arg Asp Asn Ser Lys Asn
 65                  70                  75                  80
Thr Val Tyr Leu Gln Met Asn Ser Leu Arg Ala Glu Asp Thr Ala Thr
                 85                  90                  95
Tyr Tyr Cys Ala Ser Arg His Met Arg Arg Ala Pro Trp Ser Gly Pro
                100                 105                 110
Gly Met Ser Tyr Trp Gly Gln Gly Thr Gln Val Thr Val Ser Ser
                115                 120                 125
```

<210> SEQ ID NO 14
<211> LENGTH: 121
<212> TYPE: PRT
<213> ORGANISM: Artificial sequence
<220> FEATURE:
<223> OTHER INFORMATION: Single-Domain Antibody 8

<400> SEQUENCE: 14

```
Met Ala Glu Val Gln Leu Gln Ala Ser Gly Gly Gly Phe Val Gln Pro
 1               5                  10                  15
Gly Gly Ser Leu Arg Leu Ser Cys Ala Ala Ser Gly Thr Thr Ser Gly
                 20                  25                  30
Gln Thr Ala Met Gly Trp Phe Arg Gln Ala Pro Gly Lys Glu Arg Glu
                 35                  40                  45
Phe Val Ser Ala Ile Ser Gly His His Thr Pro Arg Ala Tyr Tyr Ala
         50                  55                  60
Asp Ser Val Lys Gly Arg Phe Thr Ile Ser Arg Asp Asn Ser Lys Asn
 65                  70                  75                  80
Thr Val Tyr Leu Gln Met Asn Ser Leu Arg Ala Glu Asp Thr Ala Thr
                 85                  90                  95
```

Tyr Tyr Cys Ala Trp Ile Arg Arg Lys Pro Gln Ser Trp Tyr Trp Gly
            100                 105                 110

Gln Gly Thr Gln Val Thr Val Ser Ser
        115                 120

<210> SEQ ID NO 15
<211> LENGTH: 127
<212> TYPE: PRT
<213> ORGANISM: Artificial sequence
<220> FEATURE:
<223> OTHER INFORMATION: Single-Domain Antibody 9

<400> SEQUENCE: 15

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Ser Gly
            20                  25                  30

His Tyr Ser Met Gly Trp Phe Arg Gln Ala Pro Gly Lys Glu Arg Glu
        35                  40                  45

Phe Val Ser Ala Ile Ser Gly Arg Gly Asn Ser Leu Ser Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Trp Trp His Arg Asp Ser His Pro Gln Ser Gly Lys
            100                 105                 110

His Met Arg Tyr Trp Gly Gln Gly Thr Gln Val Thr Val Ser Ser
        115                 120                 125

<210> SEQ ID NO 16
<211> LENGTH: 121
<212> TYPE: PRT
<213> ORGANISM: Artificial sequence
<220> FEATURE:
<223> OTHER INFORMATION: Single-Domain Antibody 10

<400> SEQUENCE: 16

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Ser Lys
            20                  25                  30

Ile Thr Ser Met Gly Trp Phe Arg Gln Ala Pro Gly Lys Glu Arg Glu
        35                  40                  45

Phe Val Ser Ala Ile Ser Trp Ser Asn Gly Leu Thr Asn Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Ser Lys Ile His Thr Lys Pro Lys Trp Tyr Trp Gly
            100                 105                 110

Gln Gly Thr Gln Val Thr Val Ser Ser
        115                 120

<210> SEQ ID NO 17
<211> LENGTH: 124
<212> TYPE: PRT

<213> ORGANISM: Artificial sequence
<220> FEATURE:
<223> OTHER INFORMATION: Single-Domain Antibody 11

<400> SEQUENCE: 17

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Phe Thr Ser Glu
            20                  25                  30

Ser Thr Ser Met Gly Trp Phe Arg Gln Ala Pro Gly Lys Glu Arg Glu
        35                  40                  45

Phe Val Ser Ala Ile Ser Arg Trp Glu Ser Thr Glu Glu Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Tyr Arg Met His Trp Gly Arg Trp Arg Trp Asn
            100                 105                 110

Tyr Trp Gly Gln Gly Thr Gln Val Thr Val Ser Ser
        115                 120

<210> SEQ ID NO 18
<211> LENGTH: 15
<212> TYPE: DNA
<213> ORGANISM: Artificial Sequence
<220> FEATURE:
<223> OTHER INFORMATION: guanine-quadruplex
<220> FEATURE:
<221> NAME/KEY: misc_feature
<222> LOCATION: (1)..(15)
<223> OTHER INFORMATION: h can be A, T, or C

<400> SEQUENCE: 18
ggghggghgg ghggg                                                    15

<210> SEQ ID NO 19
<211> LENGTH: 185
<212> TYPE: PRT
<213> ORGANISM: Artificial Sequence
<220> FEATURE:
<223> OTHER INFORMATION: Single-Domain Antibody 10-01

<400> SEQUENCE: 19

Gly Arg Lys Lys Arg Arg Gln Arg Arg Pro Pro Gln Gly Gly Gly
1               5                   10                  15

Gly Ser Met Ala Glu Val Gln Leu Gln Ala Ser Gly Gly Gly Phe Val
            20                  25                  30

Gln Pro Gly Gly Ser Leu Arg Leu Ser Cys Ala Ala Ser Gly Arg Thr
        35                  40                  45

Ser Lys Ile Thr Ser Met Gly Trp Phe Arg Gln Ala Pro Gly Lys Glu
    50                  55                  60

Arg Glu Phe Val Ser Ala Ile Ser Trp Ser Asn Gly Leu Thr Asn Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Thr Tyr Tyr Cys Ala Ser Lys Ile His Thr Lys Pro Lys Trp Tyr
        115                 120                 125

```
Trp Gly Gln Gly Thr Gln Val Thr Val Ser Ser Gly Gly Gly Gly Ser
            130                 135                 140

Asn Pro Leu Gly Phe Phe Pro Gly Gly Gly Ser Asp His Gln Leu
145                 150                 155                 160

Asp Gly Gly Gly Ser Pro Lys Lys Lys Arg Lys Val Ser Ser Phe
                165                 170                 175

Leu Arg Asn His His His His His
            180                 185

<210> SEQ ID NO 20
<211> LENGTH: 185
<212> TYPE: PRT
<213> ORGANISM: Artificial Sequence
<220> FEATURE:
<223> OTHER INFORMATION: Single-Domain Antibody 10-02

<400> SEQUENCE: 20

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Ser Lys
            20                  25                  30

Ile Thr Ser Met Gly Trp Phe Arg Gln Ala Pro Gly Lys Glu Arg Glu
            35                  40                  45

Phe Val Ser Ala Ile Ser Trp Ser Asn Gly Leu Thr Asn Tyr Tyr Ala
            50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
            85                  90                  95

Tyr Tyr Cys Ala Ser Lys Ile His Thr Lys Pro Lys Trp Tyr Trp Gly
            100                 105                 110

Gln Gly Thr Gln Val Thr Val Ser Ser Gly Gly Gly Gly Ser Gly Arg
            115                 120                 125

Lys Lys Arg Arg Gln Arg Arg Arg Pro Pro Gln Gly Gly Gly Gly Ser
130                 135                 140

Asn Pro Leu Gly Phe Phe Pro Gly Gly Gly Ser Asp His Gln Leu
145                 150                 155                 160

Asp Gly Gly Gly Ser Pro Lys Lys Lys Arg Lys Val Ser Ser Phe
                165                 170                 175

Leu Arg Asn His His His His His
            180                 185
```

POLYPEPTIDES DIRECTED AGAINST VIRAL INFECTION AND USES THEREOF

CROSS-REFERENCE TO RELATED APPLICATIONS

This application is a national stage application under 35 U.S.C. 371 and claims the benefit of PCT Application No. PCT/CA2021/050234 having an international filing date of Feb. 25, 2021, which designated the United States, which PCT application claimed the benefit of priority application U.S. Provisional Application No. 62/982,474, filed Feb. 27, 2020, the disclosures of each of which are hereby incorporated herein in their entireties by reference.

REFERENCE TO SEQUENCE LISTING

This application contains a Sequence Listing submitted as an electronic text file named "11300QB-1-PUS_SequenceListing_ST25.txt", having a size in bytes of 16,636 bytes, and created on 20 Dec. 2024. The information contained in this electronic file is hereby incorporated by reference in its entirety pursuant to 37 CFR § 1.52(e)(5).

FIELD

Embodiments herein are generally related to polypeptides comprising one or more single-domain antibodies, and their methods of use, for the detection and treatment of viral infection, such as hepatitis B virus (HBV) infection. More specifically, the present polypeptides may target guanine-rich regions of viral DNA, disrupting the replication thereof.

BACKGROUND

Hepatitis B virus, herein abbreviated as HBV, is a harmful virus that causes the disease hepatitis B, an infectious disease that affects the liver. HBV is a global health problem where the virus has infected approximately two billion people worldwide. HBV infection has led to chronic hepatitis B surface antigen (HBsAg) positive infection in more than 250 million individuals, and is a major cause of hepatocellular carcinoma (HCC). The virus is also responsible for extrahepatic syndromes due to immune complex mediated systemic vasculitis leading to joint, kidney and skin disease such as polyarteritis nodosa and glomerulonephritis.

Although the development of HBV vaccines has aided in decreasing the rate of new infections, a critical number of infections still occur in underdeveloped countries, or individuals who are infected with HBV before vaccination. For instance, unvaccinated infants born to HBV infected mothers are at 50-95% risk of developing chronic hepatitis B (CHB) and have a 25-40% lifetime risk of developing serious liver diseases including HCC. HBV infection is associated with significant mortality with approximately 10-30 million new infections yearly, and of those individuals infected, approximately 1 million die annually (at a staggering rate of approximately two individuals every minute). Although approved oral therapies that are nucelos(t)ide analogs or polymerase inhibitors are effective at suppressing the virus, these drugs do not eradicate infection. Viral relapse occurs when treatment is stopped. Interferon is also approved for treatment of HBV but the drug often has severe side effects and many patients are not eligible for therapy. There remains an urgent need for new treatments for HBV and achieve a cure for chronic infection.

HBV belongs to the Hepadnaviridae family of viruses, and is classified into eight major genotypes. The HBV has a compact, partially double-stranded relaxed-circular (rc) DNA genome of ~3.2 kbp, with regions containing overlapping open reading frames and regulatory elements.

HBV primarily targets hepatocytes where HBV pre-S1 protein recognizes the sodium taurocholate cotransporting polypeptide (NTCP) bile acid receptor. Upon viral entry, the viral envelope (capsid) disintegrates and the nucleocapsid is localized into the nucleus, where the HBV rcDNA undergoes processing to synthesize a complete short strand from an incomplete strand. The resulting rcDNA with both strands of similar lengths undergoes a ligation reaction to form cccDNA that serves as a template for pregenomic RNA (pgRNA), which is exported to the cytoplasm and viral proteins are synthesized using host cell machinery. As such, the cccDNA plays an important role in the HBV life cycle, serving as a template for transcription of HBV.

To date, currently approved treatments of HBV aim to block the DNA replication at later steps in the viral life cycle. However, an infected hepatocyte can have 1-50 cccDNA copies and known therapies are, as of yet, ineffective at targeting the activity, the formation, and the destruction of the HBV cccDNA. Moreover, HBV has one of the smallest viral genomes, limiting the numbers of proteins that can be targeted for drug discovery. The resulting life-long persistence of cccDNA often leads to rebound viremia with therapy cessation. Although many drugs are being evaluated in clinical trials, most of them target viral components other than the cccDNA.

For example, several therapeutic approaches being explored are aimed at targeting viral as well as the host components. The acetylated peptides from the HBV envelope protein that block HBV entry are being investigated, and it has been shown that cell division and antiviral therapies can serve to reduce the nuclear presence of cccDNA. However, cccDNA nonetheless continues to persist, albeit at low-levels, in infected hepatocytes for years leading to HBV rebound in patients who withdraw from antiviral therapy, and in untreated persons with low-level viremia, who receive potent immunosuppression. Although several therapies are being evaluated in clinical trials, the majority of them target viral components other than the cccDNA, with the initial aim of achieving HBsAg loss or a functional cure.

A true virological cure requires targeting of cccDNA (either to destroy or inhibit its formation and/or function). Recently, the zinc finger proteins that interact with duck HBV cccDNA and suppress viral RNA transcription were evaluated. Downregulation of host transcription factors required for HBV transcription by helioxanthin analogues was suggested as one of the strategies to modulate HBV replication. CRISPR/Cas9 based studies to target cccDNA in order to reduce viral replication have been performed. However, clinical application of approaches involving downregulation of host proteins or application of CRISPR/Cas9 are limited due to their potential off-target effects.

An effective HBV vaccine is available; however, it is not useful to already infected individuals with HBV. Approved therapies for chronic hepatitis B include nucleos(t)ide analogs (requires upwards of 30 years of treatment to achieve HBsAg loss) and interferons a that are given for approximately 48 weeks of treatment but with severe side effects, and limited efficacy. Moreover, second-generation nucleos(t)ide analogs are not available in resource-poor countries. Thus, new therapies against the HBV infection are needed to help prevent the development of an end-stage liver disease.

Antibodies against many viral, human, and malignant factors have proven efficacy in the treatment of a variety of diseases. However, their large size (~150 kDa), immunogenicity, high production costs, storage and stability issues, and susceptibility to the host proteases due to the presence of flexible hinge region often limit their widespread applications. Moreover, the large size of known antibodies is also a limitation to access epitopes.

There remains a critical need for the development of new, reliable, and practical HBV cccDNA targeted therapies. It is desirable that such therapies are configured to specifically target the activity, formation, or destruction of HBV cccDNA, thereby interrupting the HBV lifecycle and eradicating HBV from infected cell.

SUMMARY

According to embodiments, at least one polypeptide and methods of use is provided, the polypeptide comprising at least one antiviral single domain antibody for targeting a guanine-rich region of viral DNA (e.g. viral covalently closed circular DNA, or cccDNA). In some embodiments, the at least one antiviral single domain antibody comprises an anti-viral single domain antibody (e.g. anti-HBV single domain antibody), and the guanine-rich region of the viral cccDNA forms a guanine-quadruplex, wherein the anti-viral single domain antibody binds the guanine-quadruplex.

In some embodiments, the present polypeptide may comprise at least one single domain antibody, the antibody comprising an anti-viral single domain antibody having an amino acid sequence selected from the group consisting of SEQ ID Nos: 9, 10, 11, 12, 13, 14, 15, 16 or 17.

In some embodiments, the present polypeptide may comprise at least one modification to include at least one coding sequence that binds at least one cell surface receptor, wherein the at least one at least one coding sequence is a sodium taurocolate cotransporting polypeptide sequence from HBV preS1 protein. In such embodiments, the at least one coding sequence is SEQ ID NO: 4 or SEQ ID NO: 5.

In some embodiments, the present polypeptide may comprise at least one modification to include at least one coding sequence that binds a cell penetrating peptide. In such embodiments, the cell penetrating peptide coding sequence is SEQ ID NO: 3.

In some embodiments, the present polypeptide may comprise at least one modification to include at least one coding sequence for cell nuclear localization. In such embodiments, the at least one nuclear localization coding sequence is SEQ ID NO: 6.

According to embodiments, a pharmaceutical composition for treating a viral infection is provided, the composition comprising at least one polypeptide comprising at least one antiviral single domain antibody for targeting a guanine-rich region of viral DNA (e.g. viral cccDNA) and a carrier. In some embodiments, the at least one antiviral single domain antibody may comprise an anti-viral single domain antibody, wherein the guanine-rich region of the viral cccDNA forms a guanine-quadruplex and the anti-HBV single domain antibody binding the guanine-quadruplex. In some embodiments, the anti-viral single domain antibody may comprise an amino acid sequence selected from the group consisting of SEQ ID NOs: 9, 10, 11, 12, 13, 14, 15, 16 or 17.

In some embodiments, the present pharmaceutical composition may comprise at least one polypeptide having at least one modification selected from the group consisting of at least one coding sequence that binds at least one cell surface receptor, at least one coding sequence that binds a cell penetrating peptide, and at least one coding sequence for cell nuclear localization. In such embodiments, the at least coding sequences may be selected from the group consisting of SEQ ID NO: 4, SEQ ID NO: 5, SEQ ID NO: 3, and SEQ ID NO: 6.

According to embodiments, methods for treating a viral infection are provided, the methods comprising administering a pharmaceutically effective amount of at least one polypeptide comprising at least one antiviral single domain antibody for targeting a guanine-rich region of viral DNA (e.g. viral cccDNA) to a subject. In some embodiments, the at least one antiviral single domain antibody comprises is an anti-viral single domain antibody (e.g. anti-HBV), wherein the guanine-rich region of the viral cccDNA forms a guanine-quadruplex and wherein the anti-viral single domain antibody binds the guanine-quadruplex to inhibit transcription of the cccDNA. In some embodiments, the anti-viral single domain antibody may comprise an amino acid sequence selected from the group consisting of SEQ ID NOs: 9, 10, 11, 12, 13, 14, 15, 16 or 17.

In some embodiments, the methods may comprise the at least one polypeptide being administered may comprise at least one modification selected from the group consisting of at least one coding sequence that binds at least one cell surface receptor, at least one coding sequence that binds a cell penetrating peptide, and at least one coding sequence for cell nuclear localization. In such embodiments, the at least coding sequence may be selected from the group consisting of SEQ ID NO: 4, SEQ ID NO: 5, SEQ ID NO: 3, and SEQ ID NO: 6.

BRIEF DESCRIPTION OF THE DRAWINGS

FIG. 3C) are shown. The last two lanes of each are PCR controls: water (-ve) and full-length HBV plasmid (+ve). Lane 1 molecular weight marker, lane 2 excess DNA that did not bind to DHX36, followed by washes and finally the elution fraction, showing cccDNA bound to DHX36 in FIGS. 3A and 3B, and unbound in FIG. 3C).

FIG. 4 provides the results of a phage ELISA assay (absorbance at 450 nm) for a plurality of single domain antibodies demonstrating their interactions with either wild-type G-quadruplex of HBV cccDNA pre-core promoter region (WT), or a mutant thereof (MUT) (FIG. 4A); and sequence listing table corresponding to sdAb 1 (SEQ ID NO: 9), sdAb 4 (SEQ ID NO: 10), sdAb 5 (SEQ ID NO: 11), sdAb 6 (SEQ ID NO: 12), sdAb 7 (SEQ ID NO: 13), sdAb 8 (SEQ ID NO: 14), sdAb 9 (SEQ ID NO: 15), sdAb 10 (SEQ ID NO: 16), and sdAb 11 (SEQ ID NO: 17) respectively (FIG. 4B).

FIG. 6 provides example modifications to the amino acid sequence of at least one of the presently selected sdAbs, according to embodiments, FIG. 6A providing one such example modification including the incorporation of coding sequences SEQ ID NO: 3 (GRKKRRQRRRPPQ), SEQ ID NO: 4 (NPLGFFP), SEQ ID NO: 5 (DHQLD), and SEQ ID NO: 6 (PKKKRKV). Herein, SEQ ID NO: 7 (GGGGS) and SEQ ID NO: 8 (SSFLRN) represent a linker and a thrombin cleavage site, respectively. SEQ ID NO: 19 is the full sequence of the sdAb 10-01 shown in the schematic and SEQ ID NO: 20 is the full sequence of the sdAb 10-02 shown in the schematic. FIG. 6B providing a schematic of the example modification shown in FIG. 6A, and FIG. 6C providing a schematic of alternative example modifications that may be made as described herein, and as may be appreciated in the art (where R and R' may either be no modification to one or more of CPP, NTCP, NLS or other sequence modifications or additions in any order, for e.g. as depicted in FIG. 6B).

DETAILED DESCRIPTION OF THE PREFERRED EMBODIMENTS

Figure 1A:
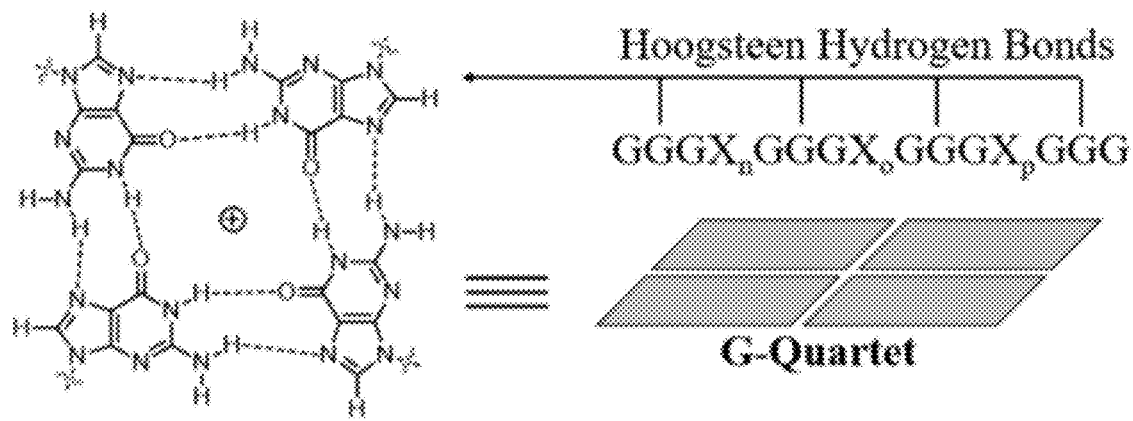
FIG. 1A (PRIOR ART) provides a schematic representation of a guanine-rich region in a gene (i.e. a region having multiple guanines), the region held together in a plane by hydrogen bonds to form a quartet, referred to as a guanine-quadruplex, or 'G-quadruplex', such as GGGXnGGGXoGGGXpGGG (SEQ ID NO: 18), wherein the n, o or p can be any of the 3 nucleotides A, T or C.

Embodiments herein are generally related to novel polypeptides specifically designed to comprise one or more single-domain antibodies and their methods of use for the detection and treatment of viral infection. More specifically, the present polypeptides may comprise one or more single domain antibodies for targeting guanine-rich regions of viral DNA, disrupting the replication of the viral DNA.

According to embodiments, the presently disclosed antiviral polypeptides and their methods of use in treating viral infections are provided based upon the discovery that a key region of the covalently closed circular DNA (e.g. Hepatitis B Virus or "HBV" cccDNA), and specifically the pre-core promoter site thereof, forms a stable, non-canonical, guanine quadruplex (referred to as the 'G-quadruplex'), and the further discovery that the G-quadruplex plays a critical role in viral replication (i.e. by interacting with host specificity proteins, e.g. Sp1). As will be shown, the foregoing discoveries have led to the design and manufacture of new, reliable, and practical polypeptides comprising at least one single domain antibody for effectively targeting the G-quadruplex structure of viral cccDNA and providing an antiviral effect by inhibiting the transcription of the viral cccDNA. It should be appreciated that embodiments herein are described using Hepatitis B Virus as the target viral DNA, the polypeptides may be specifically designed to target guanine-rich regions of other viral DNA.

Herein, novel anti-viral polypeptides comprising at least one single domain antibody and their methods of use for detecting and treating viral infection are provided. The presently disclosed polypeptides may comprise at least one anti-viral single domain antibody (e.g. anti-HBV single domain antibody) having at least one specific antigen domain for targeting the G-quadruplex of the viral DNA. The present polypeptides may comprise at least one single domain antibody having only the antigen binding domain for specifically targeting the G-quadruplex of the viral cccDNA, preventing the interaction of the cccDNA with host transcription factors (e.g. Sp1). In some embodiments, the present polypeptides may comprise at least one antiviral single domain antibody having an amino acid sequence selected from the group comprising SEQ ID NO: 9-17, or an amino acid sequence having more that at least 85% identity to the amino acid sequences. It should be understood that a nucleic acid sequence complementary to the presently disclosed anti-viral polypeptides may also have an antiviral effect against various viruses, including HBV.

TERMINOLOGY AND DEFINITIONS

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

"Affinity" refers to the strength of the sum total of non-covalent interactions between a single binding site of a molecule (e.g., an antibody) and its binding partner (e.g., an antigen). "Binding affinity" refers to intrinsic binding affinity between members of a binding pair (e.g., antibody and antigen). Affinity can be measured by common methods known in the art, including those described herein.

"Hepatitis B infection" or "HBV infection," as used herein, refers to the presence in humans of the hepatitis B virus, and is intended to include a short-term or acute infection, a long-term or chronic infection, and a dormant or latent infection (i.e., occult hepatitis B).

"HBV vaccine," as used herein, refers to a preparation that elicits an acquired immune response to HBV and can include both a prophylactic vaccine (i.e., a vaccine administered to a subject not infected with HBV for prophylaxis), or a therapeutic vaccine (e.g., a vaccine administered to a subject already infected with HBV for treatment of the infection).

"Pharmaceutical composition" or "composition" or "formulation" refers to a preparation in a form that allows the biological activity of the active ingredient(s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Single domain antibody" (sdAbs) refers to a molecule comprising one or more polypeptide chain that specifically binds to, or is immunologically reactive with, a particular antigen. Exemplary antibodies include those single domain antibodies whose complementary determining regions are part of a single domain polypeptide including, but not limited to, heavy chain antibodies, antibodies devoid of light chains, single domain antibodies derived from conventional 4-chain antibodies, engineered antibodies and single domain scaffolds other than those derived from antibodies. Single domain antibodies may be any of the art, or any future single domain, and may be derived from any species including, but not limited to, mouse, human, camel, llama, goat, rabbit, or bovine. Single-domain antibodies (sdAbs) are generally known to be small in size (approximately 15 kDa) and can be developed to target key antigen-binding domains. sdAbs can be stable under extreme pH and high-temperature conditions, and can be used in difficult host environments, such as the respiratory and gastrointestinal tracts. Moreover, sdAbs can be delivered using various routes of administration as well as directly at the site of viral infection. As would be appreciated, single-domain antibodies overcome many of the challenges associated with full-length antibodies and are thus being investigated for many viral infections. According to embodiments, an anti-HBV polypeptide is provided, wherein at least one single domain antibody, or nanobody 'NB', corresponds to an amino acid sequence represented by SEQ ID NOs: 9-17 as shown in Table 1 and as further outlined herein (e.g. SEQ ID NOs: 9-17 FIG. 4 wherein SEQ ID NO: 9 corresponds to sdAb 1; SEQ ID NO: 10 corresponds to sdAb 4; SEQ ID NO: 11 corresponds to sdAb 5; SEQ ID NO: 12 corresponds to sdAb 6; SEQ ID NO: 13 corresponds to sdAb 7; SEQ ID NO: 14 corresponds to sdAb 8; SEQ ID NO: 15 corresponds to sdAb 9; SEQ ID NO: 16 corresponds to sdAb10 and SEQ ID NO: 17 corresponds to sdAb11).

"Subject" or "subject in need" or "patient", as used herein, refers to an individual with the presence of persistent HBV cccDNA including, without limitation, an HBV infection, such as an HBV carrier, one with chronic HBV infection, or one with HBV persistence. In some embodiments, for example, the subject is a human.

"Therapeutically effective amount," as used herein, refers to the amount of an active ingredient or agent (e.g., a pharmaceutical composition) to achieve a desired therapeutic or prophylactic result, e.g., to treat or prevent a disease, disorder, or condition in a subject. In the case of an HBV infected person, the therapeutically effective amount of the therapeutic agent is an amount that reduces, inhibits, and/or relieves to some extent one or more of the symptoms associated with the HBV infection, including the viral load of HBV, and/or the amount of viral antigens detectable in the subject.

"Treatment," "treat", or "treating" refers to clinical intervention in an attempt to alter the natural course of a disorder in a subject being treated and can be performed during the course of clinical pathology. Desired results of treatment can include, but are not limited to, preventing occurrence or recurrence of the disorder, alleviation of symptoms, diminishment of any direct or indirect pathological consequences of the disorder, decreasing the rate of progression, or amelioration of a disease state, and remission or improved prognosis. For example, treatment of HBV infection can include administration of a therapeutically effective amount of a pharmaceutical composition comprising an antibody, including a single-domain antibody, to a subject to delay the development of, slow progression of, or eradicate an HBV infection.

The present polypeptides and their methods of use will now be described having regard to FIGS. 1-13.

By way of explanation, the transcription of pregenomic RNA (pgRNA) from HBV covalently closed circular DNA (cccDNA) requires the assistance of many host transcription factors, including Sp1. Sp1 is critical for the expression of genes involved in cell proliferation and is overexpressed in many cancers, including hepatocellular carcinoma (HCC). Three main binding sites for Sp1 on HBV cccDNA have been identified (preS1, preS2/S, and enhancer II promoters), resulting in positive transcription of the HBV core, pre-core and other genes, confirming a critical role of Sp1 in the HBC life cycle.

Figure 1B:
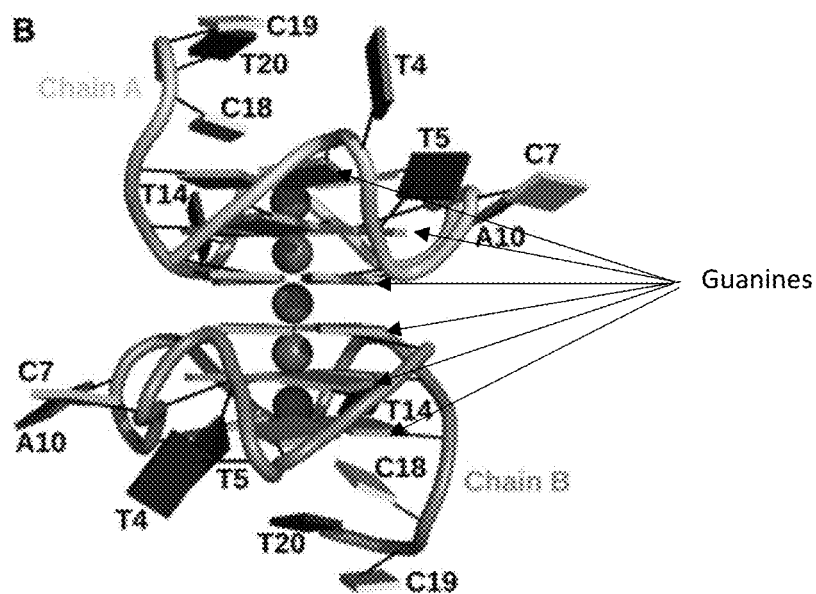
FIG. 1B (PRIOR ART) provides a cartoon representation of a high-resolution structure of a dimeric G-quadruplex from human telomerase, wherein a first monomer is presented as Chain A in the top structure of FIG. 1B and a second monomer is presented as Chain B in the bottom structure of FIG. 1B. Bases are presented in cartoon blocks, with guanines labeled with arrows. The potassium ions are shown as spheres.

In the double helix DNA according to the Watson-Crick model, adenine pairs with thymine and guanine pairs with cytosine by hydrogen bonds. However, having regard to FIGS. 1A and 1B (PRIOR ART), according to Hoogsteen, where DNA or RNA comprise a guanine-rich region having four guanines, a multiple-stranded structure is adopted to form a planar quartet, or 'G-quartet', held together by hydrogen bonds (i.e. by hydrogen bonds between faces of adjacent guanines). Three or more consecutive G-quartets stack vertically on top of each other, forming a guanine-quadruplex, or 'G-quadruplex', with such structures being stabilized by monovalent cations that occupy the central channel between the structures (FIG. 1B). The G-quadruplex structures can either adopt a parallel (i.e. where G-quartet strands run in the same direction), or antiparallel (i.e. where G-quartet strands run in alternate directions), or a hybrid thereof (for e.g., where three G-quartet strands run in one direction and the fourth strand runs in the opposite direction).

According to embodiments, methods of analyzing key regions of Sp1 binding sites of HBV cccDNA are provided, such methods comprising the step of identifying at least one conserved guanine-rich sequence in the pre-core promoter region of the viral cccDNA. As would be appreciated, multiples methods of detecting and identifying the presence of the guanine-rich sequence, and further to confirm that said guanine-rich sequence forms a quadruplex structure, may be employed.

Figure 2:
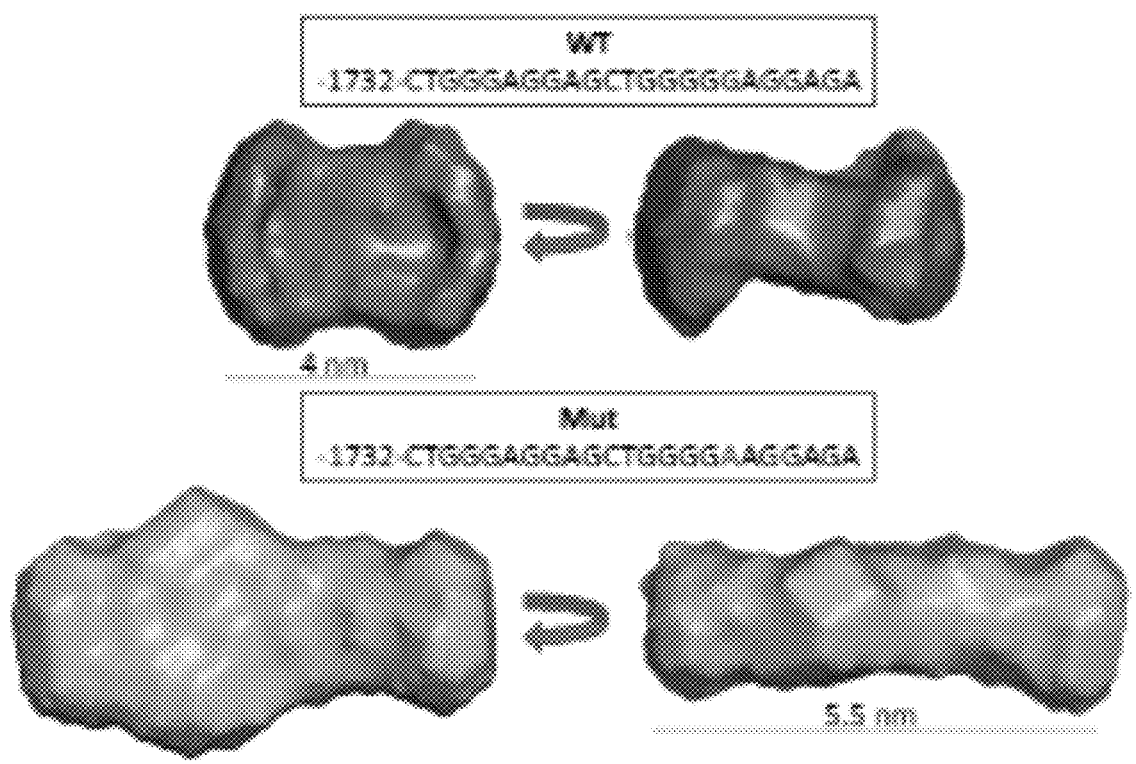
FIG. 2 provides a graphical representation of the wild-type sequence (SEQ ID NO: 1) from cccDNA pre-core promoter forming a guanine-quadruplex (top), and a graphical representation of a mutation (G1748A; SEQ ID NO: 2) disrupting said guanine-quadruplex resulting in an elongated structure (bottom).

Having regard to FIG. 2, methods are provided to detect and identify that guanine-rich sequences in the pre-core region of HBV cccDNA adopts a quadruplex structure in vitro. For example, in some embodiments, a first method of detecting and identifying the presence of a guanine-rich sequence in the HBV cccDNA in vitro comprises the step of synthesizing the 23-nucleotide sequences of wild-type (WT; SEQ ID NO: 1) and its mutant version (SEQ ID NO: 2), based on the sequence present in the pre-core region of cccDNA and the G-quadruplex, using known protocols. The low-resolution 3-dimensional structures of the sequences were studied using small-angle X-ray scattering (SAXS) allowing for the determination of the shape of biomolecules and their complexes at ~10 to 30 Å resolution. As shown in FIG. 2, the WT sample are adopts a compact structure with a length of 4 nm (FIG. 2, top), whereas a substitution of G1748 with A (SEQ ID NO: 2) results in an elongated shape with a length of 5.5 nm (FIG. 2, bottom).

In some embodiments, a second method of detecting and identifying the presence of a guanine-rich sequence in the HBV cccDNA in vitro comprised the use of circular dichroism (CD) experiments using known protocols, such methods also confirming significant differences in secondary structures of WT and mutant samples, and that a parallel complex is formed.

Accordingly, the presently described SAXS and CD methods provide confirmation that the guanine-rich region of the pre-core promoter region of the cccDNA forms a G-quadruplex in vitro.

Figure 3:
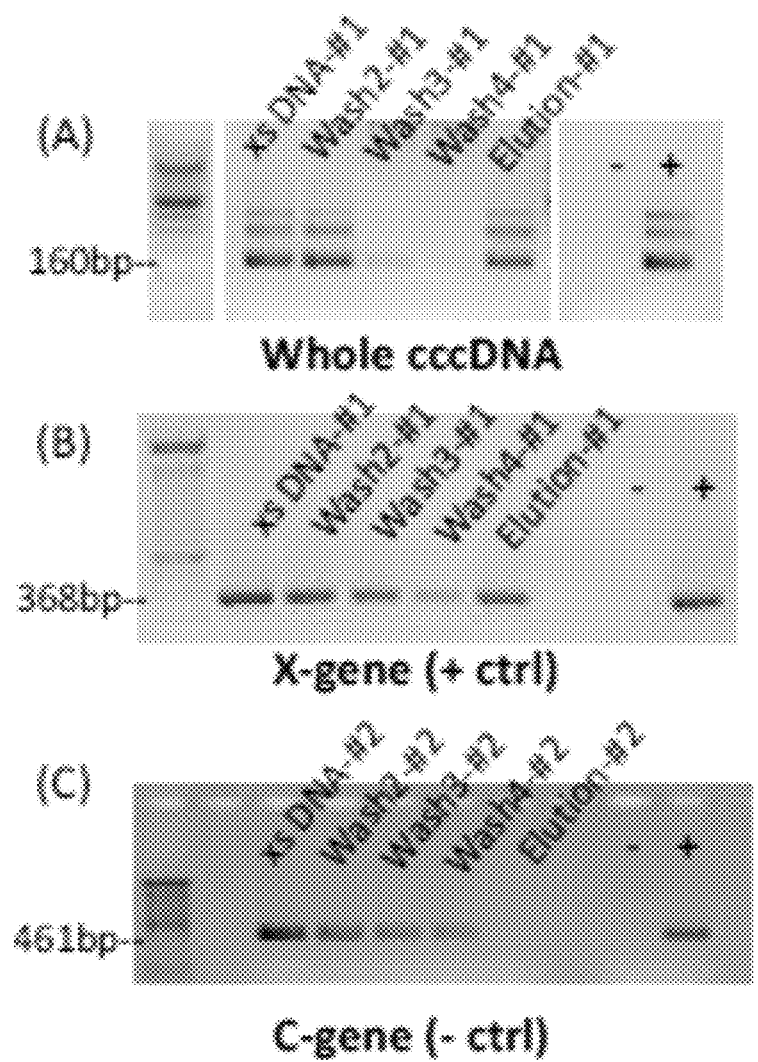
FIG. 3 provides the results of pulldown assays using a guanine-quadruplex binding protein, DHX36, wherein pulldown of whole cccDNA are extracted from explanted HBV infected liver samples (FIG. 3A), amplified regions of HBV from a lab-based plasmid with segments accounting for X-gene (FIG. 3B) and C-gene segments (negative control.

Having regard to FIG. 3, methods are provided to detect and identify that guanine-rich sequences in the pre-core region of HBV cccDNA adopts a quadruplex structure in vivo. For example, in some embodiments, methods comprise performing a pulldown assay of entire viral cccDNA extracted from explanted patient-derived liver samples according to known protocols (e.g. HBV-infected explant liver from a transplant patient suffering from HBV-related liver disease).

In some embodiments, such assays may be performed utilizing a known G-quadruplex binding protein, such as DHX36 protein. Such G-quadruplex binding protein may be tagged using a hexa-histidine (His6) tag. As would be known in the art, such hexa-histidine (His6) tagged DHX36 may be expressed and purified, and then immobilized on beads coated with nickel ions that bind with His6-tag. The Hirt-extracted cccDNA was then incubated with the DHX-36 bound beads. After washing, DXH36 was eluted, and the cccDNA from the patient-derived samples were detected, as shown in FIG. 3A. As would be appreciated, having regard to FIG. 3B, the foregoing assays were repeated to ensure that the DHX36 binds with the cccDNA only by recognizing the G-quadruplex from the pre-core region, such assays using polymerase chain reaction (PCR)-amplified regions of HBV genome from laboratory-based plasmids having segments accounting for an X-gene region that houses the G-quadruplex (FIG. 3B). As would further be appreciated, having regard to FIG. 3C, the foregoing assays were also repeated using PCR-amplified regions of HBV genome from laboratory-based plasmids having segments accounting for a C-gene segments where the G-quadruplex is absent (i.e. negative control).

Accordingly, the presently described pulldown assay methods provide confirmation that the guanine-rich sequence from the pre-core promoter region of the HBV cccDNA forms a G-quadruplex in vivo (i.e. in HBV-infected hepatocytes, as per interacting protein DXH36).

In some embodiments, methods are provided to detect and confirm the presence of the above-identified G-quadruplex in different HBV genotypes. For example, in some embodiments, an analysis of known HBV patient databases may be performed (i.e. publicly available HBV Patient Database; hbvdb.ibcp.fr) to verify that the G-quadruplex of the HBV cccDNA region is present in all major HBV genotypes, confirming that the region is critical for transcription of viral cccDNA (e.g. for pre-core RNA). Accordingly, the foregoing discovery of the presence of the G-quadruplex structure, and its interaction with host transcription factors, provides a suitable target for therapeutic compositions serving to interrupt a main cause of viral infection—i.e. the transcription of viral cccDNA. Moreover, the foregoing discovery of the presence of the G-quadruplex structure in all major HBV genotypes, and the ability of the presently designed at least one polypeptide to target same, may also provide an efficient and effective diagnostic tool for detecting the presence of cccDNA in clinical samples. Finally, as would be understood that because the sequence of the identified G-quadruplex differs vastly from the consensus sequences that Sp1 typically recognizes in the host genome, the presently designed polypeptides targeting said G-quadruplex are less likely to produce off-target effects.

As will be described in more detail, at least one polypeptide comprising at least one single domain antibody and its methods of use for inhibiting the transcription of viral cccDNA are provided. More specifically, the at least one polypeptide comprising at least one single domain antibody for targeting binding between viral cccDNA and host transcription factors are provided, wherein such binding may occur between a guanine-rich region of the viral cccDNA (e.g. the pre-core promoter region of the HBV cccDNA) and the host transcription factors. In some embodiments, the at least one polypeptide comprising at least one single domain antibody may inhibit binding between the G-quadruplex structure of the HBV cccDNA and the host transcription factors (e.g. host transcription factor Sp1).

By way of explanation, antibodies against many viral, human, and malignant factors have proven efficacy in the treatment of a variety of diseases. However, known full-length antibodies suffer various setbacks as a result of, without limitation, their large size (~150 kDa), immunogenicity, high production costs, storage and stability issues, and susceptibility to the host proteases due to the presence of flexible hinge regions often limit their widespread application. Large size is also a limitation to access epitopes.

In contrast, single domain antibodies (sdAbs) are smaller (~15 kDa) and only comprise the antigen-binding domain, overcoming the major challenges associated with full-length antibodies. The absence of antibody Fc-region also prevents antibody-dependent enhancement, a common immunopathological consequence. Due to their stability under extreme pH and high-temperature conditions, sdAbs are ideal candidates for the development of therapeutic pharmaceutical compositions that target challenging host environments such as the respiratory and gastrointestinal tracts, through various routes of administration, as well as directly at the site of viral infection.

According to embodiments, methods of developing and designing the present at least one novel polypeptide comprising at least one antiviral sdAb are provided. In some embodiments, the methods comprise accessing a fully synthetic phage-display library that codes for 3-billion sdAbs clones, enabling efficient selection of in vitro humanized antibodies against virtually any antigen. Advantageously, no animals or immunization are required, allowing the selection of sdAbs that can target unprocessed G-quadruplex, thereby overcoming conventional techniques of injecting animals to raise antibodies (such techniques known to alter antigen structures).

Having regard to FIG. 4A, the foregoing methods were used to detect at least nine (9) polypeptides having at least one sdAb with a higher affinity for the wild-type G-quadruplex structure of the HBV cccDNA as compared to the mutant G-quadruplex structure. Having regard to FIG. 4B and Table 1 herein, the at least nine polypeptides having at least one sdAb are referred to as sdAbs 1, 4, 5, 6, 7, 8, 9, 10, and 11 and comprise an amino acid sequence represented as SEQ ID NOs: 9, 10, 11, 12, 13, 14, 15, 16, and 17, respectively. At least one (1) polypeptide that failed to interact with pre-core G-quadruplex of cccDNA was also developed, such polypeptides having at least one sdAb being operative as a control (e.g., sdAbcon).

According to embodiments, the detected polypeptides having at least one sdAb were expressed and purified for characterization purposes, such expression and purification methods being optimized so as to evaluate the detected at least one polypeptides for use in antiviral treatment. In some embodiments, expression and purification methods were optimized using, for example, a His$_6$-tag affinity chromatography and SEC to remove aggregated or degraded material.

Figure 5A:
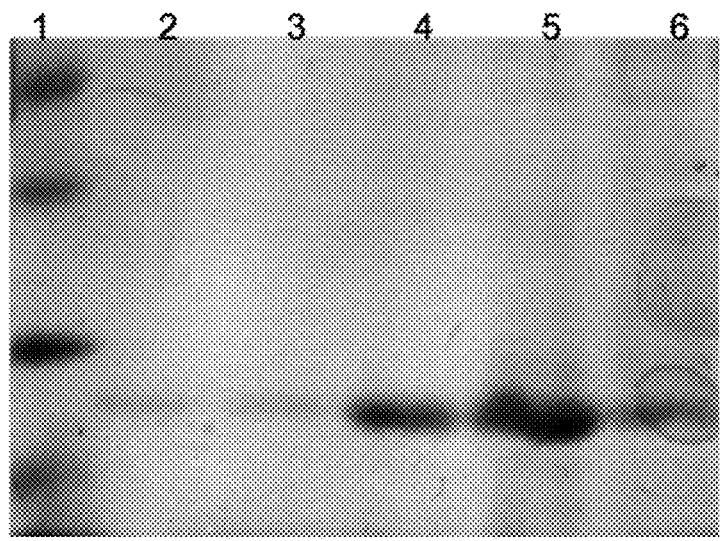
FIG. 5A demonstrates an SDS-PAGE (sodium dodecyl sulphate-polyacrylamide gel electrophoresis) analysis of an example purified single domain antibody (sdAb11) according to embodiments herein, where lane 1 represents standard molecular weight marker whereas elution fractions are shown in lanes 2-6, indicating the presence of sdAbs (Mw of 15 kDa) between 18.4 kDa and 14.4 kDa markers.
Figure 5B:
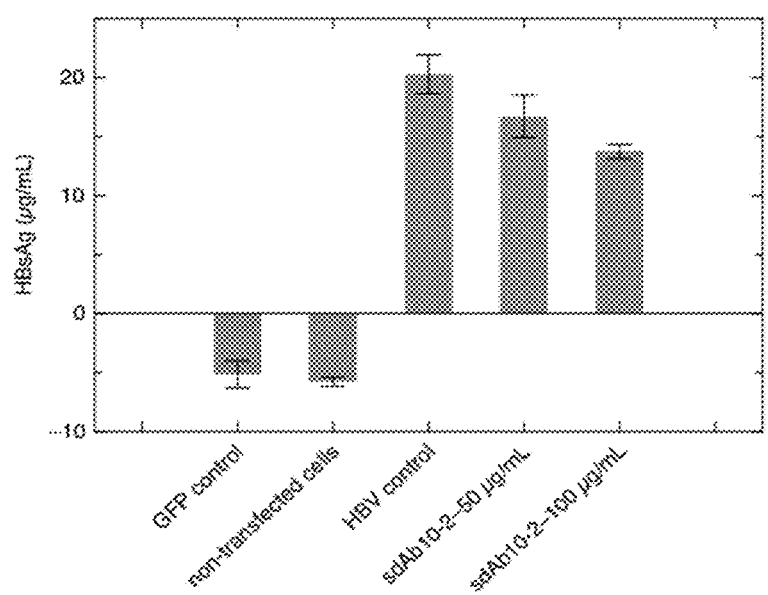
FIG. 5B demonstrates the targeting of the present single-domain antibodies by a dose-dependent decrease in HbSAg levels.

Having regard to FIG. 5A, expression methods using a bacterial expression system (SDS-PAGE) yielded ~3 mg of pure sdAbs from 1 L bacterial culture, where lane 1 represents the standard molecular weight marker and elution fractions are shown in lanes 2-6, indicating the presence of at least one polypeptides having at least one sdAb (between 18.4 kDa and 14.4 kDa markers). Having regard to FIG. 5B, characterization methods demonstrate that the presently detected at least one polypeptide effectively targets and binds the HBV surface antigen (HBsAg), with the concentration of HBsAg following exposure to the polypeptides decreases in a dose-dependent manner (e.g. example data from a polypeptide comprising sdAb10 shown). That is, a dose-dependent decrease in HBsAg levels occurred with increased concentration of a polypeptide comprising sdAb10 (from 50 μg/mL to 100 μg/mL). The foregoing confirms that the at least one polypeptide comprise at least one antiviral sdAb.

According to embodiments, methods of developing and designing the present at least one novel polypeptide comprising at least one antiviral sdAb further included the modification of the at least one polypeptide were modified as a means for improving the therapeutic efficacy thereof. For example, in some embodiments, one or more coding plasmids of the at least one polypeptide having at least one sdAb were modified to improve antiviral properties.

In some embodiments, modifications of the present at least one polypeptide comprised, but is not limited to, the incorporation of any one or more coding sequences operative to improve access of the at least one polypeptide to the viral cccDNA. In some embodiments, modifications of the present at least one polypeptide may comprise incorporating at least one coding sequence operative to aid the polypeptides in accessing various targets of a hepatocyte. In some embodiments, modifications of the present at least one polypeptide may comprise incorporating at least one coding sequence operative to aid the polypeptides in binding hepatocyte cell surface receptors, in binding at least one hepatocyte cell penetrating peptide, in targeting the nuclei of the hepatocyte (i.e. to provide improved hepatocyte nuclear localization), and/or a combination thereof. It should be appreciated that any of modifications to the at least one polypeptide described herein is for explanatory purposes only, and that any modification serving to, without limitation, improve or strengthen the affinity, solubility, and/or stability of the at least one polypeptide having at least one antiviral sdAbs is contemplated.

By way of example, methods of developing and designing the present at least one novel polypeptide comprising the modification of at least one polypeptide having at least one antiviral sdAb is provided (e.g. sdAb10; SEQ ID NO: 16). Herein, sdAb10 was selected as an example due to its homologous structure, said structure aligning well with the other polypeptides having a higher binding affinity for HBsAgs. It should be appreciated, however, that any of the at least one selected polypeptide having at least one sdAb may be so modified. It should also be contemplated that any of the at least one selected polypeptide may comprise a nascent polypeptide and may be modified in any manner known in the art to achieve the antiviral properties described herein.

In some embodiments, having regard to FIG. 6A, the at least one modification of the selected polypeptide (e.g. sdAb10) may comprise incorporating at least one coding sequence operative to aid the polypeptide in binding at least one hepatocyte cell surface receptor, such as a peptide from HBV preS1 proteins. The at least one hepatocyte cell surface receptor may comprise, without limitation, sodium taurocholate cotransporting polypeptide (NTCP), and the coding sequence may comprise an NTCP-recognition sequence from HBV preS1 protein. In such embodiments, the coding sequences may be selected from SEQ ID NO: 4 and SEQ ID NO: 5.

In some embodiments, modification of the at least one polypeptide sdAb10 may comprise incorporating a coding sequence operative to provide hepatocyte nuclear localization. In such embodiments, the at least one nuclear localization coding sequence may comprise SEQ ID NO: 6.

In some embodiments, modification of the at least one polypeptide sdAb10 may comprise any number and/or combination of further modifications aiding in the targeting the viral cccDNA, and specifically the G-quadruplex pre-core promoter region of HBV cccDNA. For example, having regard to FIG. 6B, modification of the at least one polypeptide sdAb10 may comprise, without limitation, the incorporation of coding sequences for various peptides allowing for selective targeting of hepatocytes, for achieving a certain degree of movement within the targeted hepatocytes, for increasing the spatial separation between domains, as well as for improving solubility and folding of the at least one therapeutic peptides (e.g., including NTCP-recognition sequences, cell penetration peptide sequences "CPP", nuclear localization peptide sequences "NLS", etc.).

In some embodiments, modification of the at least one polypeptide sdAb10 may comprise such further modifications as, without limitation, the incorporation of coding sequences for at least one linker (e.g. peptides used for single-chain variable fragment as well as other proteins, including poly-glycine-serine), for at least one thrombin cleavage site, and/or a combination thereof. For example, modification of the at least one polypeptide sdAb10 may comprise, without limitation, at least one linker (standard generic spacer sequence) having sequence SEQ ID NO: 7, such modification being devisable from previously engineered proteins including an Fc domain of IgG linked with a C-terminal domain of agrin protein via a poly-glycine-serine linker. In some embodiments, modification of the at least one polypeptide sdAb10 may comprise, without limitation, at least one thrombin cleavage side having sequence SEQ ID NO: 8.

Figure 7:
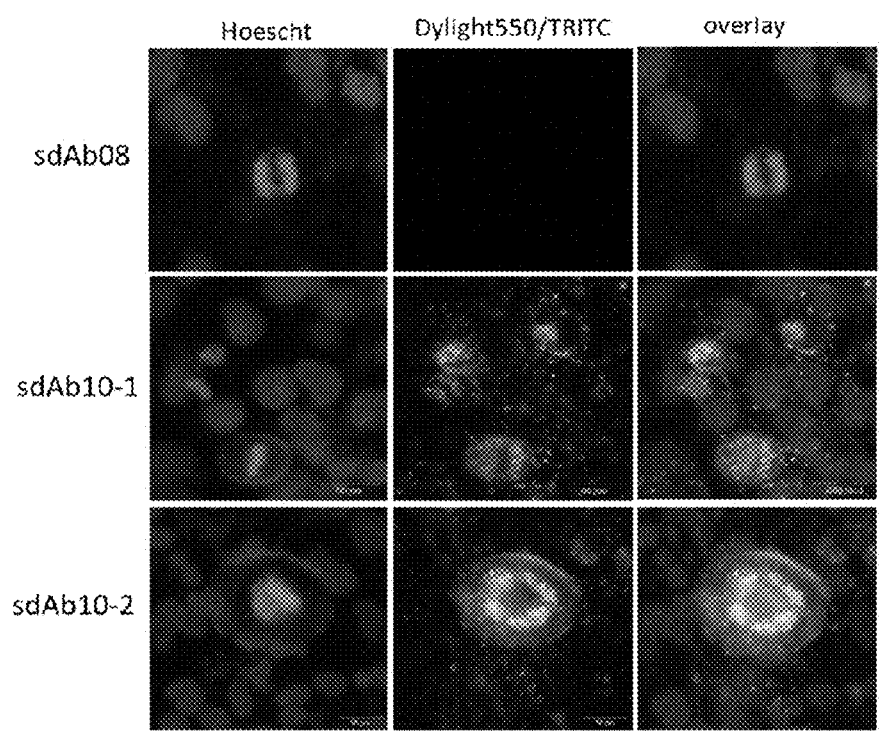
FIG. 7 provides data showing that modifications of the amino acid sequence of at least one presently selected polypeptides shown in FIG. 6A resulted in the at least one polypeptide localizing and penetrating into target cells (e.g. NTCP-HUH7 cells), where the modified at least one polypeptide (sdAb10-1 and sdAb10-2) enter the cell compared with unmodified polypeptides that do not enter the cells (sdAb08).

The foregoing one or more modifications of the at least one polypeptide sdAb10 result in antiviral efficacy. For example, having regard to FIG. 7, where the at least one polypeptide is modified to comprise an NTCP-recognition sequence from HBV preS1 protein (e.g. sdAb10-1 and sdAb10-2), the modified polypeptides localize and enter the target hepatocyte cells (e.g. NTCP-HUH7 cells), where unmodified polypeptides fail to do so (e.g. sdAb08). More specifically, the first row shown in FIG. 7 provides that polypeptide sdAb08, which was not modified to include a cell penetrating peptide coding sequence, failed to enter target cells (and was washed away during the peptide-staining process). Alternatively, the second and third rows shown in FIG. 7 provide that both polypeptides modified to include a cell penetrating peptide coding sequence entered the target cells (i.e. the nuclei and cytoplasm being visualized Hoescht stain and by fluorescently labelled anti-vinculin antibodies, respectively).

According to embodiments, it should be contemplated that the present methods for developing and designing the present at least one novel polypeptide may comprise modifying said polypeptides so as to evaluate their targeting of cccDNA within liver cells, and the role of sdAbs-pre-core-G-quadruplex interactions in HBV replication. For example, high-resolution structural information could be used to provide structure-guided modifications to therapeutic compositions, for example to increase solubility and/or affinity thereof. The presently developed polypeptides may be selected based upon their solubility and affinity with pre-core G-quadruplex, and their affinity with pre-core G-quadruplex could be improved by identifying the interacting site between the polypeptides and the G-quadruplex structure (e.g. using structural-biophysical methods where cccDNA is present). The at least one polypeptide may then be further expressed and purified, along with the G-quadruplex structure using synthetically designed oligonucleotides. Such designed peptides could then be interacted with the G-quadruplex structure to form 'sdAbs-G-quadruplex complexes', with such complexes being purified using SEC to remove any unbound species and to obtain a monodispersed complex preparation.

Low-resolution structures of the sdAbs-G-quadruplex complexes could be determined using SAXS, as described above. A highly pure preparation of the sdAbs-G-quadruplex complexes could be used to set-up crystallization trials using commercially available kits, followed by optimization of conditions, as described above. Results may be collected using at least one diffractometer (e.g. University of Lethbridge, Alberta, Canada, the Canadian Light Source, University of Saskatoon, Saskatchewan, Canada), as known in the art. Computational studies, using a commercially available package (e.g. Schrödinger Suites), on the high resolution structural information of the sdAbs-G-quadruplex complexes could also be used to, where applicable, change, add, and/or remove particular amino acids at the pre-core G-quadruplex binding site, as a means for optimizing the binding affinity between the HBV pre-core G-quadruplex and the sdAbs. Docking studies may also be performed.

The resulting information obtained from an analysis of at least one 'best candidate' polypeptides, whereby the polypeptides are modified to optimize binding affinities, can lead to the development of additional constructs using at least some or all of the above-mentioned peptide sequences. For example, because the cDNA constructs for these sequences are <525 nucleotides, the cDNA constructs cloned into a plasmid of interest using a commercial supplier (e.g. Genewiz) can be readily performed.

The present at least one polypeptides and methods of use will now be illustrated in more detail by way of the following Examples.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1—Analysis of the Present at Least One Polypeptide Having at Least One Antiviral sdAb and Binding of Same to HBV cccDNA G-Quadruplex, Forming HBV-Pre Core G-Quadruplex-sdAbs Complexes By way of background, eastern North American woodchucks (*Marmota monax*) infected with the woodchuck hepatitis virus (WHV) provide a virologically and pathogenically relevant model of human HBV infection, chronic hepatitis B (CHB), and HBV-induced HCC. Similarities of the WHV model include virus genome structure, sequence homology (overall 65% but exceeding 70% in some genes), ultrastructure, antigenic cross-reactivity, and liver disease, including acute hepatitis progressing to chronic hepatitis and HCC. WHV infection, like HBV, causes high rates of chronic hepatitis (85%) and almost always leads to HCC. Moreover, the sequence alignment for the HBV and WHV pre-core promoter regions suggests that both viruses have similar G-rich regions. Hence, it is known that woodchucks can be used to demonstrate the localization of sdAbs and their possible role in WHV replication.

In this Example, binding studies for at least one of the presently designed polypeptides having at least one sdAb (e.g. sdAb10M and sdAb1) with HBV pre-core G-quadruplex were performed. Having regard to FIG. 8A, HBV pre-core G-quadruplex interacted with sdAB10M with an affinity Kd of 260 nM, whereas the negative control polypeptide (sdAb1) did not interact with HBV pre-core G-quadruplex. MST studies suggested that the present polypeptides interact with the pre-core G-quadruplex with high affinity (Kd of 260±4.2 nM), compared to a similar sequence from human genome (Kd of 1.6±0.02 µM). This binding was also confirmed using sdAb1 (FIG. 4), said control polypeptide being tested for its ability to bind with the pre-core G-quadruplex and, as expected, it did not interact with G-quadruplex.

In this Example 1, binding studies for at least one of the presently designed polypeptides having at least one sdAb with HBV pre-core G-quadruplex were performed using patient derived samples. For example, two of the presently developed sdAbs, namely sdAb #8 (NB01) and sdAb #1 (NB07), were produced via *E. coli* expression system and purified via nickel bead affinity chromatography, then size exclusion chromatography (as described in more detail herein). Pulldown assays using Hirt-extracted cccDNA from explanted liver tissue (i.e. liver transplanted secondary to HCC from HBV) were performed.

Figure 8A:
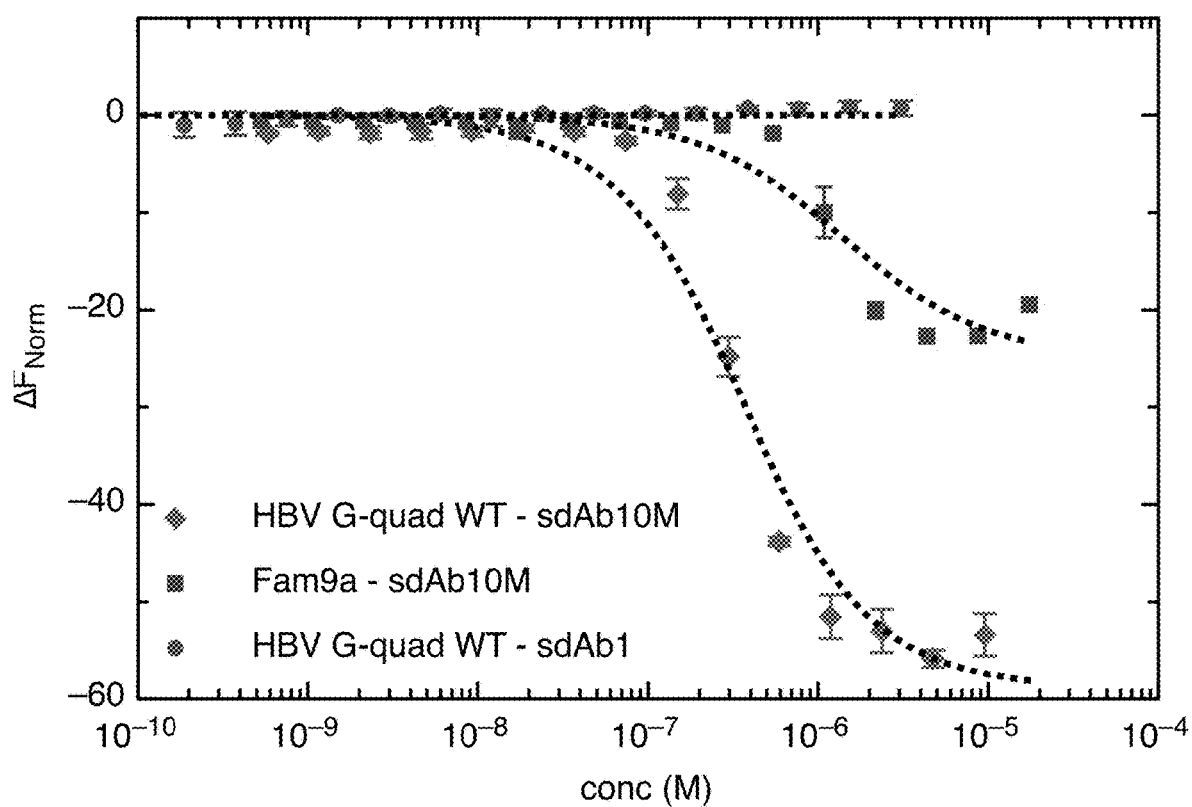
FIG. 8 provides data showing that modifications of the amino acid sequence of at least one presently selected polypeptides shown in FIG. 6A resulted in the at least one polypeptide having anti-HBV effects, with MST study data showing the modified at least one polypeptide (sdAb10-M) binds with a G-quadruplex region of HBV cccDNA pre-core promoter region (FIG. 8A), and with pulldown assay results showing that the modified at least one polypeptide (sdAb8) interacts with HBV cccDNA (as compared to unmodified sdAb1.
FIG. 8B).
Figure 8B:
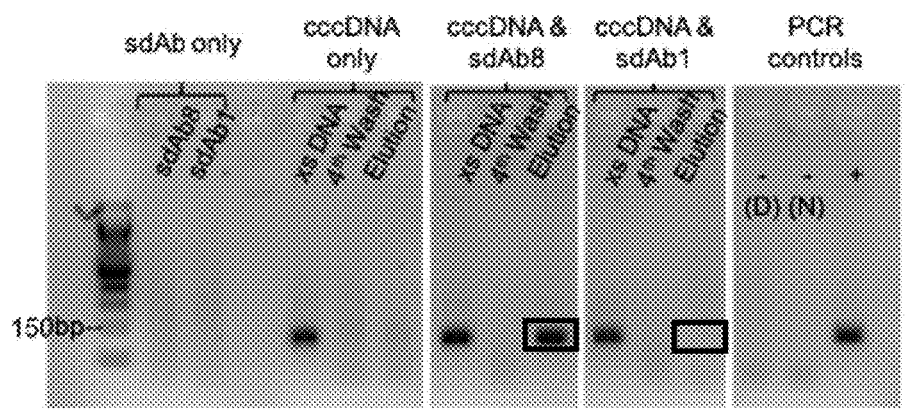

Having regard to FIG. 8B, results are provided from the pulldown study using sdAbs-bound to magnetic nickel beads with Hirt-extracted, T5 exonuclease-digested cccDNA from an explanted HBV infected liver. Beads were incubated with the corresponding sdAbs comprising, in this Example, the presently developed sdAb8 and sdAb1, washed, and incubated with cccDNA. Excess cccDNA was removed ("xsDNA" lanes), followed by 4 washing steps ("4th Wash" lanes). The sdAbs were eluted and cccDNA was detected through nested PCR ("Elution" lanes). The first lane is the DNA marker highlighting the 150 bp fragment and the next two lanes represent the "sdAb only" elutions (sdAb8 and sdAb1). Subsequent sets of 3 represent the excess cccDNA ("xs"), last washes ("W") and elutions ("E") from the corresponding tubes. The last three lanes represent the PCR controls, with negatives from the direct (D) and nested (N) rounds. The results show two of the three replicates from sdAb8 picked up cccDNA (i.e. demonstrating a good binder, black box), while none of the replicates from the sdAb1 picked up cccDNA (i.e. demonstrating a poor binder, negative control, black box). The present data confirms that at least one of the presently developed polypeptides, namely, sdAb8 interacts with cccDNA as compared to sdAb1, which only weakly interacted with the G-quadruplex (FIG. 4) and did not interact with cccDNA.

Figure 9:
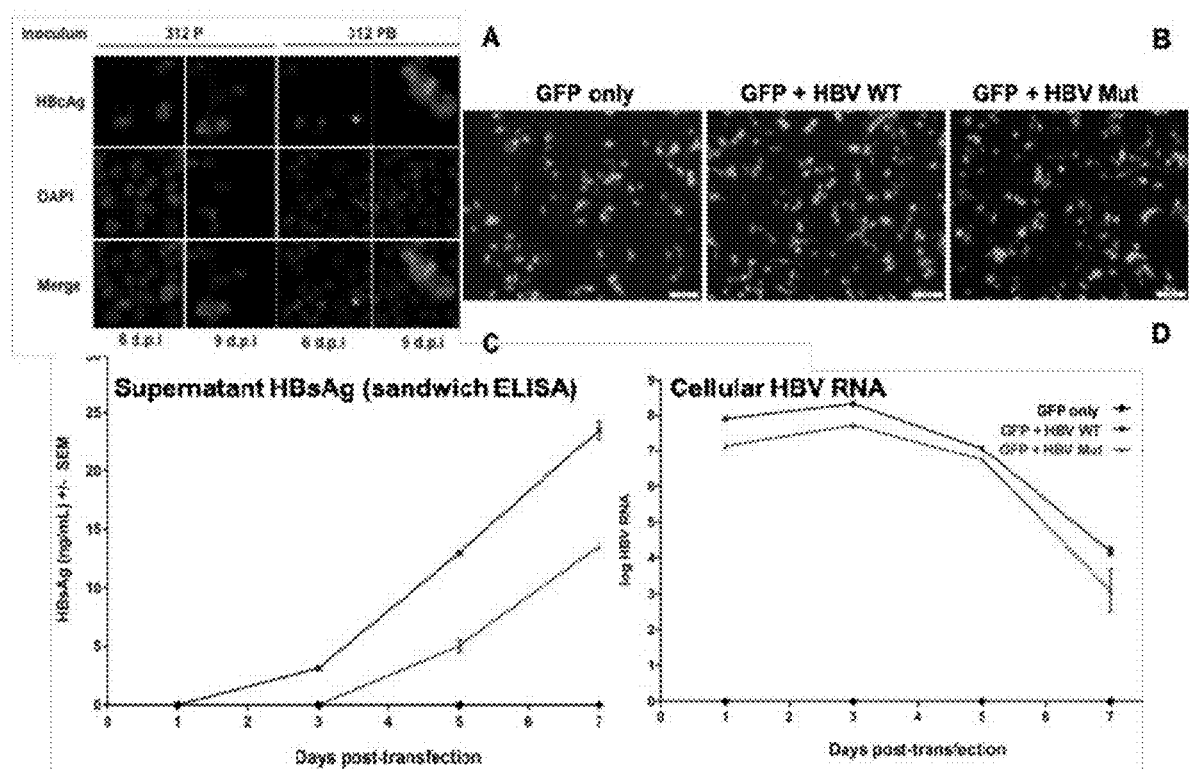
FIG. 9 shows HepaRG cells infected with paired plasma (P)- and PBMC (PB)-derived HBV inoculum of CHB carriers (ID ##312 and 316) and immune-stained with a rabbit polyclonal antibody against HBcAg (Panel A), wherein primary antibody was detected by FITC labeled goat anti-rabbit IgG (HBcAg) and the cell nucleus was stained with DAPI; the HepG2 cells transfected with either GFP-pcDNA, or HBV WT/Mut plasmid expressing GFP (Panel B); and the detection of HBsAg and HBV RNA for cells infected with either GFP, GFP+HBV WT or GFP+HBV Mut plasmid (Panels C and D). Cells were visualised using a fluorescence microscope.

FIG. 9 shows the role of the presently described sdAbs in hepadnaviral replication in HepaRG cells infected with clarified plasma-derived HBV virions. After the appropriate incubation period, the supernatant was removed, cells were washed, and total nucleic acid was extracted to quantify HBV replication. Viral DNA and RNA was analyzed in the cells and their supernatants using quantitative PCR, and the viral proteins (HBeAg, HBsAg) were detected by sandwich ELISA.

In order to determine if the modified sdAbs (for specifically targeting the hepatocytes and for nuclear localization) are localized inside the hepatocyte nucleus, the modified sdAbs were first tagged with green fluorescent protein (GFP). Unmodified sdAbs that did not contain cell-penetration, preS1 and nuclear localization peptides was used as a negative control. Additionally, because HepG2 cells do not express NTCP receptors, and require HBV plasmid transfection to establish HBV infection, HepG2 cells were used as a negative control for HepaRG cells. The cells were treated with GFP-labelled modified and unmodified sdAbs. The nucleus and cytoplasm were visualized using widely-used DAPI stain (4',6-diamidino-2-phenylindole, interacts with adenine-thymine rich regions in DNA, e.g. FIG. 9, panel A) and by fluorescently labelled anti-vinculin antibodies, respectively. The results show that only the modified sdAbs localize in the nucleus of HepaRG cells. Without being limited to theory, it may be that entry of the presently developed unmodified sdAbs or modified sdAbs into the cells may either occur through passive diffusion or active transport via one or more alternative transport mechanisms.

It is believed that the NTCP receptor is critical for HBV to enter the human hepatocytes. However, WHV may not utilize NTCP receptor to enter woodchuck hepatocytes. In order to analyse the foregoing, it is contemplated that the asialoglycoprotein receptor (referred to herein as "ASGPR"), typically expressed in abundance on human and woodchuck hepatocytes, could be targeted. The ASGPR binds with sugars, such as pullulan, which is widely used for targeted drug delivery to liver. Therefore, pullulan, with the high-affinity sdAb and sdAbcon could be attached to the presently developed sdAbs to provide pullulan-linked sdAbs.

Accordingly, this Example 1 establishes that that the presently developed sdAbs can be localized in the nuclei of hepatocyte-based cell lines, demonstrating functionality in vitro. Herein, the presently developed sdAbs provide a pharmaceutically effective composition for use in targeting HBV cccDNA, thereby disrupting and preventing hepadnaviral replication.

Example 2—Analysis of Toxicity and/or Potential Side Effects of the Present at Least One Polypeptide One of the challenges faced by therapeutics during the preclinical stage is altered conformational stability, which may affect their binding with a target molecule. To ensure that the presently designed polypeptides, apart from their high-affinity for pre-core G-quadruplex, meets key criteria of stability and storage, thermal stability and solubility studies of the polypeptides were performed by detecting the intrinsic fluorescence from tryptophan and tyrosine residues (which will indicate transitions in the folding state of said polypeptides using a Tycho NanoTemper™ instrument).

Figure 10:
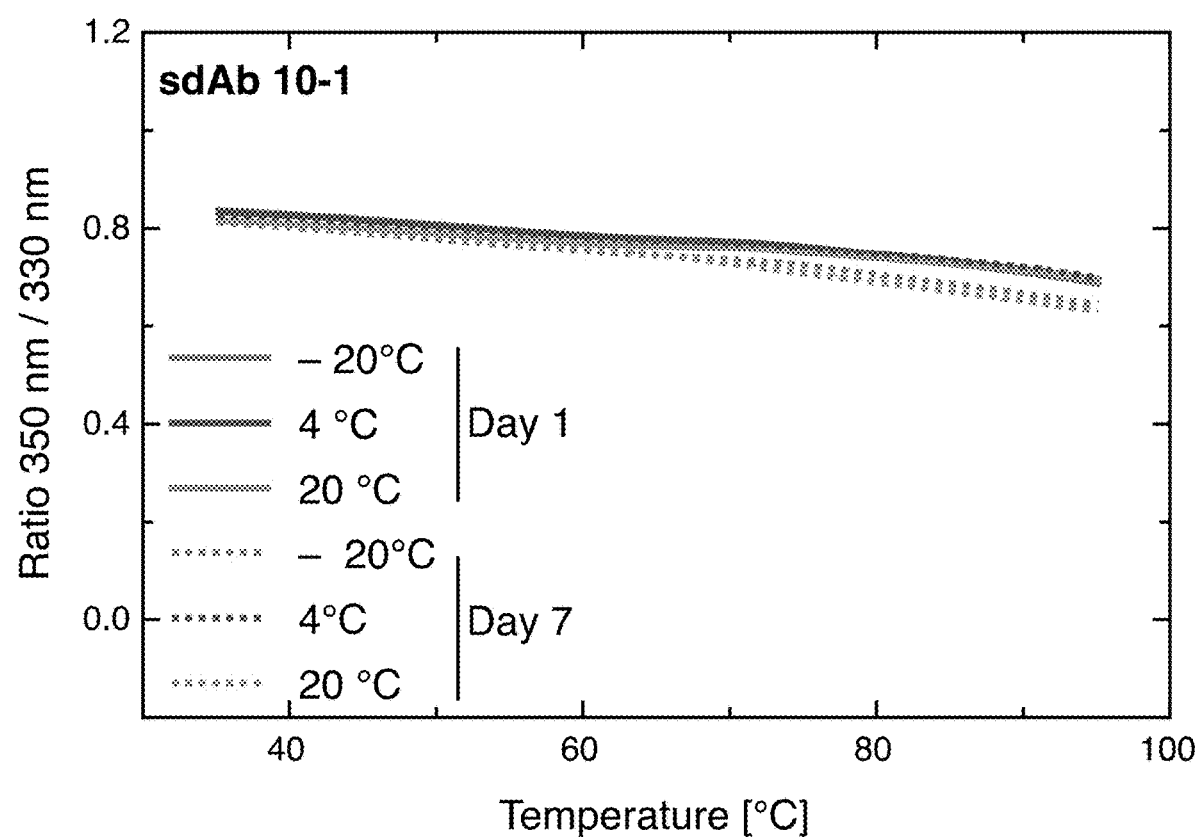
FIG. 10 provides results of a stability study confirming that the at least one presently selected polypeptides are stable at room temperature, at 4° C., and at −20° C.

Having regard to FIG. 10, stability studies of the presently designed polypeptides performed over 7 days confirm that said polypeptides are stable at room temperature, at 4° C., and at −20° C.

In order to evaluate whether the at least one presently selected polypeptide causes drastic negative effects on human cells, cell-viability assays of the purified G-quadruplex-binding polypeptides were performed with liver-derived cell lines (HepG2 and HBV infected HepAD38). Briefly, HepAD38 cells were plated in 96-well plates (10,000 cells/well) without tetracycline to induce HBV expression for 3 days. After 3 days, tetracycline was added to the medium to aid HBV transcription from the cccDNA genome and not plasmid. Alamar blue dye protocol was used to assess cell viability, and the data provided is the result of 3 technical replicates. Throughout the present assays, Tenofovir Disoproxil Fumurate (TDF), a potent nucleotide analogue (and an approved drug) that is being used for the treatment of HBV and HIV, was used. The assays were restricted to the highest concentration of Tenofovir to ~0.3 µM, considering its clinically-relevant concentration of ~0.1 µM.

Figure 11:
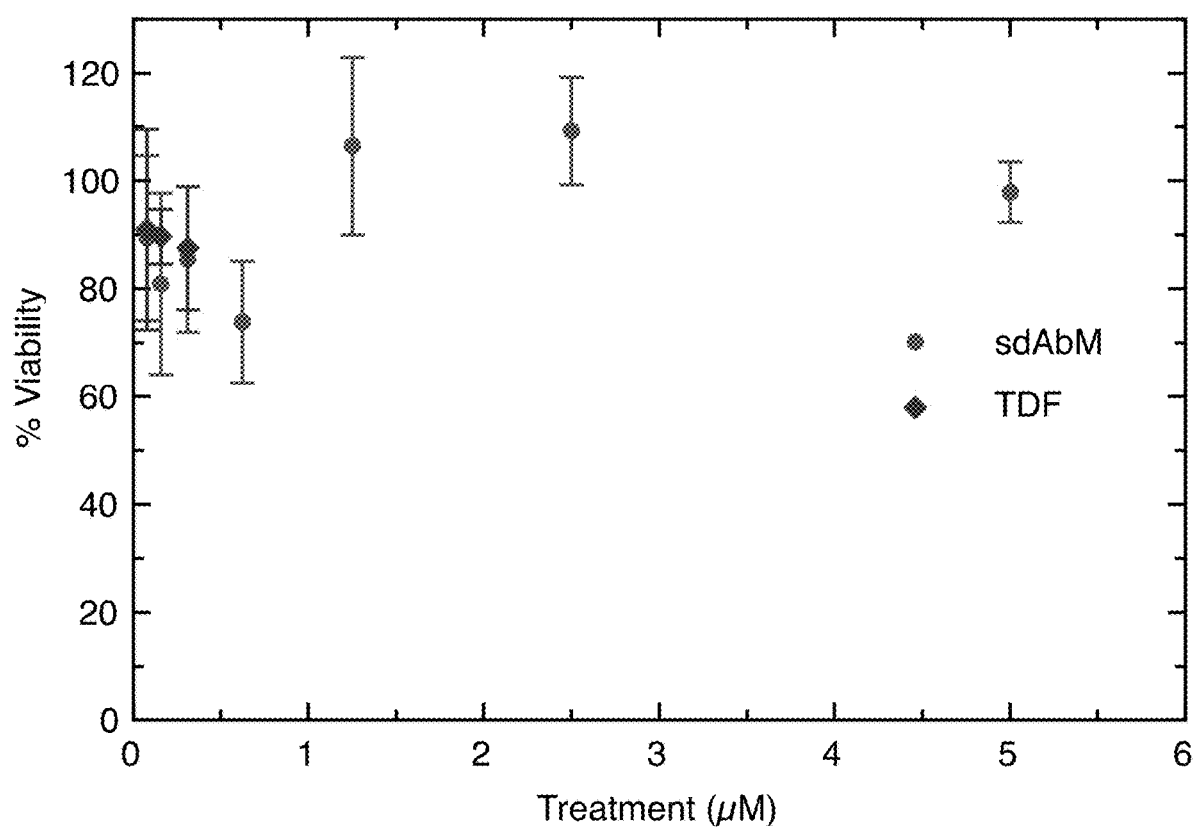
FIG. 11 provides results of a cell-viability assays showing that the at least one presently selected polypeptides are not toxic to human cells.

Having regard to FIG. 11, cell viability assays show that the presently designed polypeptides are not toxic to HepAD38 cells up to 5 µM, a significantly higher concentration compared to the $K_d$ (250 nM) of said polypeptide with its target.

Example 3—Analysis of the Effect of the Present at Least One Polypeptide on cccDNA Stability/Activity By way of explanation, HBV "e" antigen (HBeAg) is an excreted form of the core protein that can be measured in the blood of infected individuals as a surrogate marker for cccDNA activity. High levels of HBeAg indicate active viral replication, while low levels indicate suppression of cccDNA activity. Since the presently designed polypeptides target the cccDNA PreC/C promoter (responsible to produce pregenomic RNA, core protein, and e antigen transcripts) HBeAg can be used as a surrogate marker for anti-cccDNA activity.

In this Example 3, the effects of the presently designed polypeptides on HBV replication were analyzed, HepAD38 cells that expresses HBV under the control of a tetracycline promoter were used. HepAD38 cells were plated in the presence of TDF or candidate therapeutic (sdAb10-2) without tetracycline for three days to induce HBV production and to establish a cccDNA reservoir in the nuclei of infected cells. After three days, drugs/sdAbs were replenished and the media was replenished with tetracycline to suppress HBV transcripts being produced from the plasmid, so that only HBV markers be produced from the established cccDNA reservoir. Varying drug concentrations of—TDF and sdAb10-2 were used to determine drug toxicity (TD50) and efficacy during the 6-day time course.

Figure 12:
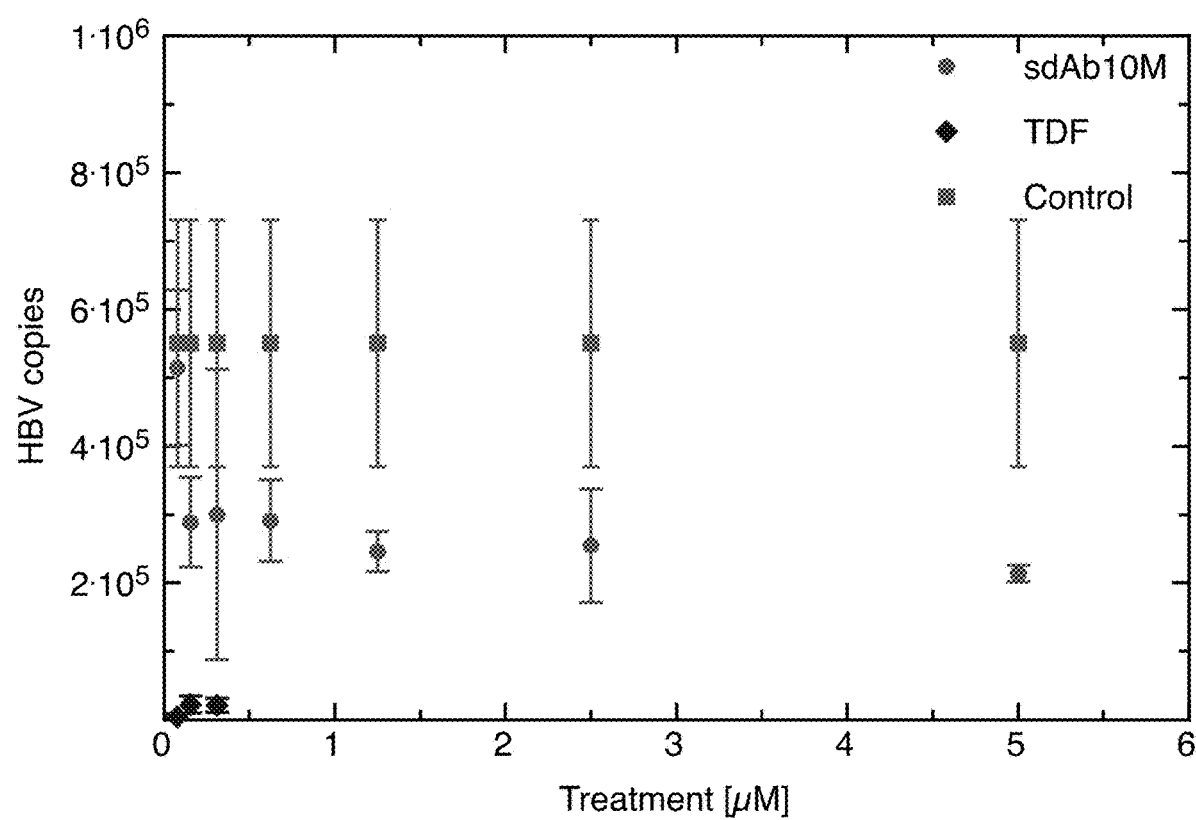
FIG. 12 demonstrates the reduction of supernatant viral cccDNA upon exposure to or treatment with the at least one presently selected polypeptides.
Figure 13:
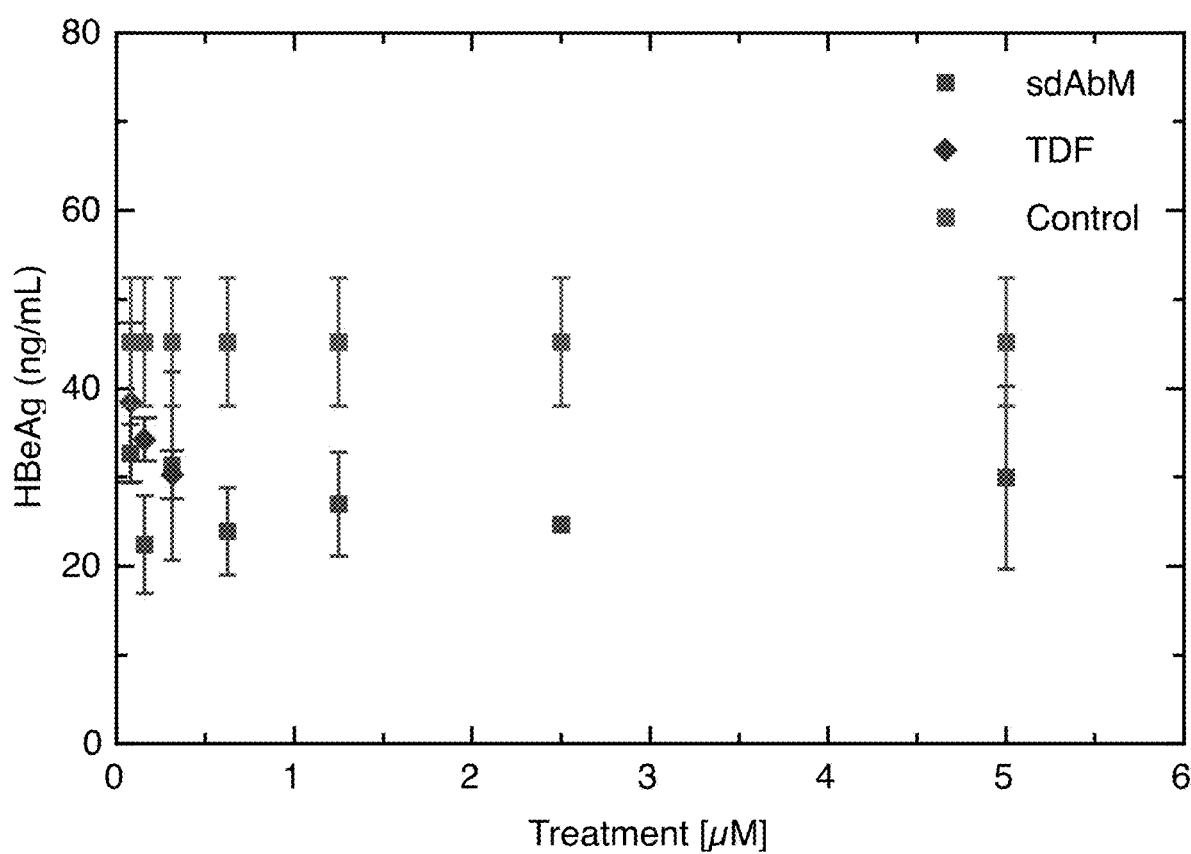
FIG. 13 demonstrates the reduction of viral antigens, namely, HBeAg levels upon exposure to or treatment with the at least one presently selected polypeptides.

Having regard to FIG. 12, TDF targets the HBV reverse transcriptase, thus only affecting the number virions secreted in the supernatant. In contrast, the presently designed polypeptides should affect cccDNA stability, which can be indirectly measured through levels. As expected, a significant decrease in supernatant HBV (2 log) was caused by TDF treatment. A significant, albeit lower, decrease in HBV supernatant DNA was also observed from sdAb10-2 treatment (0.5 log).

The ability of the presently designed polypeptides to reduce HBeAg levels was also analyzed. Having regard to FIG. 13, since TDF only affects the reverse transcriptase and not cccDNA, HBeAg levels did not significantly decrease. In contrast, treatment with sdAb10-2 significantly decreased HBeAg levels, which demonstrates an effect on cccDNA activity. The significant reduction in supernatant HBV and HBeAg levels indicate that sd10-2 affects cccDNA stability/activity.

It is important to note that HBeAg is transcribed from the same ORF as HBV pre-genomic RNA (pgRNA). As presented in FIG. 13, HBeAg level is significantly reduced upon sdAb treatment, which may imply that sdAbs, in addition to cccDNA stability can also impact pgRNA transcription. Note that HBV-infected patients often require-TDF as life-long treatment and it does not target the root-cause of persistent infection—HBV cccDNA. On the other hand, sdAbs we develop target cccDNA and provide an opportunity for a virological cure. It is may not achieve virological cure based on monotherapy in all patients, especially with high cccDNA levels. However, a combination of an approved drug (e.g. TDF) and sdAbs has the potential to cure HBV infection.

According to embodiments of the present disclosure, methods of using the present at least one polypeptide having at least one antiviral sdAbs may comprise a diagnostic tool for the screening and/or detection of viral cccDNA in clinical samples, either in vitro or in vivo. Advantageously, due to the manufacture and production cost for the present polypeptides using bacterial host is significantly lower compared to that of monoclonal antibodies which require the application of highly sophisticated animal cell-culture facilities, the presently disclosed polypeptides are also useful in assessing viral cccDNA generally.

According to embodiments, for clinical use, the present at least one polypeptide may be administered alone via any suitable administration route effective to achieve a desired therapeutic result or may be formulated into pharmaceutical composition. In some embodiments, methods for treating viral infection may comprise administering to a subject in need thereof a therapeutically effective amount of the present at least one polypeptide. In other embodiments, methods for treating viral infection may comprise administering to a subject in need thereof a pharmaceutical composition comprising a therapeutically effective amount of the present at least one of the polypeptides and a pharmaceutically acceptable carrier. In yet other embodiments, methods for treating viral infection may comprise administering to a subject in need thereof a pharmaceutical composition comprising a therapeutically effective amount of the present at least one of the polypeptides and at least one a pharmaceutically approved therapeutic agent or drug, such agent or drug serving to provide an additive and/or synergistic benefit. Administration to a subject in need of the at least one polypeptide in accordance with the present methods of treatment may provide a therapeutic effect that protects the subject from and/or treats the progression of a viral infection.

In some embodiments, the present pharmaceutical composition and methods of use may comprise administering the present at least one polypeptide to a subject in need thereof by any mode of administration that delivers the polypeptide systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

In some embodiments, the present pharmaceutical compositions and methods of use comprise administering a pharmaceutically effective amount of the compositions to a subject in need thereof by at least one appropriate mode of delivery selected from, but not limited to, the group consisting of intraperitoneally, intravenously, percutaneously, sublingually, intramuscularly, intranasally, subcutaneously, by injection, infusion, instillation, and inhalation. For example, without limitation, administration by injection can include intramuscular, intravenous, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion. In some embodiments, the subject is a viral carrier, and may be a subject with chronic viral infection, or a subject with viral persistence.

In some embodiments, the present pharmaceutical compositions and methods of use may comprise formulating at least one of the presently developed polypeptides in the manufacture or preparation of a medicament for the treatment of a viral infection. In a further embodiment, the medicament is for use in a method for treating a viral infection comprising administering to a subject in need thereof an effective amount of the medicament. In certain embodiments, the medicament further comprises an effective amount of at least one additional therapeutic agent or drug, or treatment. In a further embodiment, the medicament is for use in treating viral infection in a subject comprising administering to the subject an amount effective of the medicament to treat the viral infection.

For the treatment of a viral infection, polypeptides and nucleic acids according to embodiments herein may be administered to a subject by conventional routes, such as intravenously. However, the appropriate dosage of the present at least one polypeptide contained in the compositions and formulations of the present disclosure (when used alone or in combination with one or more other additional therapeutic agents) will depend on factors including the severity and course of the disease, whether the antibody is administered for preventive or therapeutic purposes, the previous therapy administered to the subject, the subject's clinical history and response to the antibody, and the discretion of the attending physician. It is contemplated that the present pharmaceutical compositions may be administered to the subject in need thereof more than once a day, at least once a day, at least once a week, or at least once a month. Various dosing schedules including, but not limited to single or multiple administrations over various time points, bolus administration, and pulse infusions are contemplated.

It should be understood that Sp1 also interacts with G-quadruplexes in human genome, and modules gene expression during early development, cell proliferation, and oncogenesis. However, the Sp1 target sequence of the HBV pre-core G-quadruplex differs from its corresponding target sequence identified for the human genome. Moreover, the HBV pre-core G-quadruplex sequence herein only partially matches with a DNA sequence on human chromosome 8, indicating that the risk of cross-reactivity of sdAbs that targets HBV cccDNA is low.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and the described portions thereof.

TABLE 1

SEQUENCE LIST

| SEQ ID NO: | SEQUENCE |
|---|---|
| 1 | -1732-CTGGGAGGAGCTGG GGGAGGAGA |
| 2 | -1732-CTGGGAGGAGCTGG GGAAGGAGA |
| 3 | GRKKRRQRRRPPQ |
| 4 | NPLGFFP |
| 5 | DHQLD |
| 6 | PKKKRKV |
| 7 | GGGGS |
| 8 | SSFLRN |

TABLE 1-continued

SEQUENCE LIST

| SEQ ID NO: | SEQUENCE |
|---|---|
| 9 | MAEVQLQASGGGFVQPGGSL RLSCAASGRTYRHSGMGWFR QAPGKEREFVSAISDDHNME SYYADSVKGRFTISRDNSKN TVYLQMNSLRAEDTATYYCA MTKWHGPGGPHWYWGQGTQV TVSS |
| 10 | MAEVQLQASGGGFVZPGGSL RLSCAASGRTSKWYSMGWFR QAPGKEREFVSAISYRQNIR AYYADSVKGRFTISRDNSKN TVYLQMNSLRAEDTATYYCA ATHSYLFKFPTHFPQPQDYW GQGTQVTVSS |
| 11 | MAEVQLQASGGGFVZPGGSL RLSCAASGRTSYHTNMGWFR QAPGKEREFVSAISSSPNAA TYYADSVKGRFTISRDNSKN TVYLQMNSLRAEDTATYYCA RTKYGRVMGHMWYWGQGTQV TVSS |
| 12 | MAEVQLQASGGGFVQPGGSL RLSCAASGTGFRHTAMGWFR QAPGKEREFVSAISGHASKQ AYYADSVKGRFTISRDNSKN TVYLQMNSLRAEDTATYYCA FRRAEKIYGHPMAPQKLWYW GQGTQVTVSS |
| 13 | MAEVQLQASGGGFVQPGGSL RLSCAASGRTYRGETMGWFR QAPGKEREFVSAISWGWSNR AYYADSVKGRFTISRDNSKN TVYLQMNSLRAEDTATYYCA SRHMRRAPWSGPGMSYWGQG TQVTVSS |
| 14 | MAEVQLQASGGGFVQPGGSL RLSCAASGTTSGQTAMGWFR QAPGKEREFVSAISGHHTPR AYYADSVKGRFTISRDNSKN TVYLQMNSLRAEDTATYYCA WIRRKPQSWYWGQGTQVTVS S |
| 15 | MAEVQLQASGGGFVQPGGSL RLSCAASGRTSGHYSMGWFR QAPGKEREFVSAISGRGNSL SYYADSVKGRFTISRDNSKN TVYLQMNSLRAEDTATYYCA WWHRDSHPQSGKHMRYWGQG TQVTVSS |
| 16 | MAEVQLQASGGGFVQPGGSL RLSCAASGRTSKITSMGWFR QAPGKEREFVSAISWSNGLT NYYADSVKGRFTISRDNSKN TVYLQMNSLRAEDTATYYCA SKIHTKPKWYWGQGTQVTVS S |
| 17 | MAEVQLQASGGGFVQPGGSL RLSCAASGFTSESTSMGWFR QAPGKEREFVSAISRWESTE EYYADSVKGRFTISRDNSKN TVYLQMNSLRAEDTATYYCA YRMHWGGRWRWNYWGQGTQV TVSS |

We claim:

1. At least one polypeptide comprising at least one antiviral single domain antibody for targeting a guanine-rich region of viral DNA, wherein the at least one antiviral single domain antibody comprises an anti-Hepatitis B Virus (HBV) single domain antibody comprising amino acid sequence selected from the group consisting of SEQ ID NOs: 9, 10, 11, 12, 13, 14, 15, 16 and 17.

2. The polypeptide in claim 1, wherein the guanine-rich region of the viral DNA comprises a guanine-rich region of viral covalently closed circular DNA (cccDNA).

3. The polypeptide of claim 2, wherein the guanine-rich region of the cccDNA forms a guanine-quadruplex and the at least one single domain antibody binds the guanine-quadruplex.

4. The polypeptide of claim 1, wherein the polypeptide comprises at least one modification to include at least one coding sequence that binds at least one hepatocyte cell surface receptor.

5. The polypeptide of claim 4, wherein the at least one at least one coding sequence may comprise a sodium taurocolate cotransporting polypeptide sequence from HBV preS1 protein.

6. The polypeptide of claim 5, wherein the at least one coding sequence is SEQ ID NO: 4 or SEQ ID NO: 5.

7. The polypeptide of claim 1, wherein the polypeptide comprises at least one modification to include at least one coding sequence that binds a cell penetrating peptide.

8. The polypeptide of claim 7, wherein the cell penetrating peptide co

9. The polypeptide of claim 1, wherein the polypeptide comprises at least one modification to include at least one coding sequence for cell nuclear localization.

10. The polypeptide of claim 9, wherein the at least one nuclear localization coding sequence is SEQ ID NO: 6.

11. The polypeptide of claim 1, wherein the at least one polypeptide further comprises at least one linker, wherein the linker is SEQ ID NO: 7.

12. The polypeptide of claim 1, wherein the at least one polypeptide further comprises at least one thrombin cleavage site, wherein the at least one thrombin cleavage site is SEQ ID NO: 8.

13. A pharmaceutical composition for treating a viral infection, the composition comprising at least one polypeptide comprising at least one antiviral single domain antibody for targeting a guanine-rich region of viral DNA and a carrier, wherein the at least one antiviral single domain antibody comprises an anti-HBV single domain antibody comprising an amino acid sequence selected from the group consisting of SEQ ID NOs: 9, 10, 11, 12, 13, 14, 15, 16 and 17.

14. The pharmaceutical composition of claim 13, wherein the guanine-rich region of the viral cccDNA comprises a guanine-rich region of viral covalently closed circular DNA (cccDNA).

15. The pharmaceutical composition of claim 14 wherein the guanine-rich region of the viral cccDNA forms a guanine-quadruplex and the single domain antibody binds the guanine-quadruplex.

16. The pharmaceutical composition of claim 13, wherein the at least one polypeptide comprises at least one modification selected from the group consisting of at least one coding sequence that binds at least one cell surface receptor, at least one coding sequence that binds a cell penetrating peptide, and at least one coding sequence for cell nuclear localization.

17. The pharmaceutical composition of claim 16, wherein the at least one coding sequences are selected from the group consisting of SEQ ID NO: 4, SEQ ID NO: 5, SEQ ID NO: 3, and SEQ ID NO: 6.

18. The pharmaceutical composition of claim 13, wherein the at least one polypeptide comprises a modification selected from at least one linker consisting of SEQ-ID SEQ ID NO: 7 and at least one thrombin cleavage site consisting of SEQ ID NO: 8.

19. The pharmaceutical composition of claim 13, wherein a pharmaceutically effective amount of the composition is administered to a subject.

20. A method for treating a viral infection, the method comprising administering a pharmaceutically effective amount of at least one polypeptide comprising at least one antiviral single domain antibody for targeting a guanine-rich region of viral DNA to a subject, wherein the at least one antiviral single domain antibody comprises an anti-HBV single domain antibody comprising an amino acid sequence selected from the group consisting of SEQ ID NOs: 9, 10, 11, 12, 13, 14, 15, 16 and 17.

21. The method of claim 20, wherein the guanine-rich region of the viral DNA comprises a guanine-rich region of viral covalently closed circular DNA (cccDNA).

22. The method of claim 21, wherein the guanine-rich region of the viral cccDNA forms a guanine-quadruplex and the single domain antibody binds the guanine-quadruplex to inhibit transcription of the cccDNA.

23. The method of claim 20, wherein the at least one polypeptide comprises at least one modification selected from the group consisting of at least one coding sequence that binds at least one cell surface receptor, at least one coding sequence that binds a cell penetrating peptide, and at least one coding sequence for cell nuclear localization.

24. The method of claim 23, wherein the at least coding sequences are selected from the group consisting of SEQ ID NO: 4, SEQ ID NO: 5, SEQ ID NO: 3, and SEQ ID NO: 6.

25. The method of claim 20, wherein the at least one polypeptide comprises a modification selected from at least one linker consisting of SEQ ID NO: 7 and at least one thrombin cleavage site consisting of SEQ ID NO: 8.

* * * * *